US007341744B1

(12) United States Patent
Rozhon et al.

(10) Patent No.: US 7,341,744 B1
(45) Date of Patent: Mar. 11, 2008

(54) METHOD OF TREATING SECRETORY DIARRHEA WITH ENTERIC FORMULATIONS OF PROANTHOCYANIDIN POLYMER

(75) Inventors: Edward James Rozhon, El Granada, CA (US); Atul S. Khandwala, San Carlos, CA (US); Akram Sabouni, Fairport, NY (US); Gul P. Balwani, Fremont, CA (US); Jody Wai-Han Chan, Mountain View, CA (US); David F. Sesin, San Carlos, CA (US)

(73) Assignee: Napo Pharmaceuticals, Inc., South San Francisco, CA (US)

( * ) Notice: Subject to any disclaimer, the term of this patent is extended or adjusted under 35 U.S.C. 154(b) by 453 days.

(21) Appl. No.: 09/712,033

(22) Filed: Nov. 14, 2000

Related U.S. Application Data

(63) Continuation of application No. 09/066,989, filed on Apr. 23, 1998, now abandoned, which is a continuation-in-part of application No. 08/730,772, filed on Oct. 16, 1996, now abandoned.

(51) Int. Cl.
*A01N 65/00* (2006.01)
(52) U.S. Cl. .................. 424/725; 514/183; 514/732; 514/867
(58) Field of Classification Search ............... 424/725, 424/451, 464, 468, 474; 514/732, 867
See application file for complete search history.

(56) References Cited

U.S. PATENT DOCUMENTS

| 4,698,360 A | * | 10/1987 | Masquelier | ............ 514/456 |
|---|---|---|---|---|
| 4,857,327 A | | 8/1989 | Virdalm | |
| 5,043,160 A | | 8/1991 | Würsch | |
| 5,211,944 A | | 5/1993 | Tempesta | |
| 5,234,922 A | | 8/1993 | Welsh | |

FOREIGN PATENT DOCUMENTS

EP           481396          1/1995

OTHER PUBLICATIONS

Black, "The Prophylaxis and Therapy of Secretory Diarrhea", Medical Clinics of North America 66(3): 611-621.
Castelli and Carosi, 1995, "Epidemiology of Traveler's Diarrhea", Chemotherapy 41(suppl. 1): 20-32.
Chen et al., "Studies on the Anti-Tumor. Anti-Bacterial, and Wound-Healing Properties of Dragon's Blood", Planta Med. 60: 541-545.
Driesen et al., 1993, "Studies on Preweaning Piglet Diarrhoea", Australian Veterinary Journal, 70(7): 259-262.
DuPont, 1995, "Pathogenesis of Traveler's Diarrhea", 41(suppl 1): 33-39.
DuPont, 1995, "Traveler's Diarrhea", Infections of the Gastrointestinal Tracr, (Edited by M. Blaser et al., Raven Press, Ltd., New York): 299-310.

Gabriel et al., 1994, "Cystic Fibrosis Heterozygote Resistance to Cholera Toxin in the Cystic Fibrosis Mouse Model", Science 266: 107-109.
Gabriel et al., 1993, "CFTR and Outward Rectifying Chloride Channels Are Distinct Proteins with a Regulatory Relationship", Nature 363:263-266.
Galvez et al., 1991, "Antidiarrhoeic Activity of *Sclerocarya birrea* Bark Extract and its Active Tannin Constituent in Rats", Phyt. Res. 5: 276-278.
Galvez et al., 1993, "Pharmacological Activity of a Procyanidin Isolated from *Sclerocarya birrea* Bark: Antidiarrhoeal Activity and Effects on Isolated Guinea-pig Ileum", Phyt. Res. 7:25-28.
Gracey, 1986, "Bacterial Diarrhoea", *Clinics in Gasteroenerology* 15(1): 21-37.
Gutzwiller et al., 1996, "*Effects of Oral Lactose and Xylose Loads on Blood Glucose, Galactose, Xylose, and Insulin Values in Healthy Calves and Calves with Diarrhea*," AJVR 57(4): 560-563.
Harris, 1988, "*Review of Selected Bacterial Enterotoxins and their Role in Gastroenteritis*", 18: 102-108.
Holland, 1990, "Some Infectious Causes of Diarrhea in Young Farm Animals", *Clinical Mircobiology Reviews* 3(4): 345-375.
Hör et al., 1995, "*Inhibition of Intestinal Chloride Secretion by Proanthocyanidins from Guazuma ulmifolia*", Planta Med. 61: 208-212.
Hor et al., 1996, "Proanthocyanidin Polymers with Antisecretory Activity and Proanthocyanidin Oligomers from Guazuma Ulmifolia Bark", *Phytochemistry* 42(1): 109-119.
König et al., 1994, "Ellagitannins and Complex Tannins from Quercus petraea Bark", J. Nat. Prod. 57: 1411-1415.
Mouricout, 1991, "Swine and Cattle Enterotoxigenic *Escherichia coli*-mediated Diarrhea. Development of Therapies Based on Inhibition of Bacteria-Host Interactions", *Eur. J. Epidemiol.* 7(6): 588-604.
Newman et al., 1987, "High-Resolution C NMR Studies of Proanthocyanidin Polymers (Condensed Tannins)", *Nag. Res. Comm.* 25: 118-124.
Onwukaeme and Lot, 1991, "A Pharmacological Evaluation of Baphia nitida Lodd (Leguminosae) Ethanolic-Extracts on Rats and Mice", Phytotherapy Res. 5: 254-257.
Onwukaeme and Anuforo, 1993, "*Phytochemical and Pharmacological Studies on Pycanthus angolensis* (Welw) Warb (Myristicaceae)", Discovery and Innovation 5: 317-322.

(Continued)

*Primary Examiner*—Irene Marx
(74) *Attorney, Agent, or Firm*—King & Spalding, LLP

(57) ABSTRACT

Pharmaceutical compositions containing a proanthocyanidin polymer composition which are useful for the treatment and prevention of secretory diarrhea are provided. The invention specifically relates to pharmaceutical formulations of a proanthocyanidin polymer composition which has been isolated from a *Croton* spp. or a *Calophyllum* spp. In particular, the invention relates to a formulation of a proanthocyanidin polymer composition which protects the composition from the effects of stomach acid after oral administration, particularly to those formulations which are enteric coated. The invention also relates to methods of producing a directly compressible proanthocyanidin polymer composition, as well as compositions containing the directly compressible proanthocyanidin polymer composition.

37 Claims, 9 Drawing Sheets

OTHER PUBLICATIONS

Figure 1:
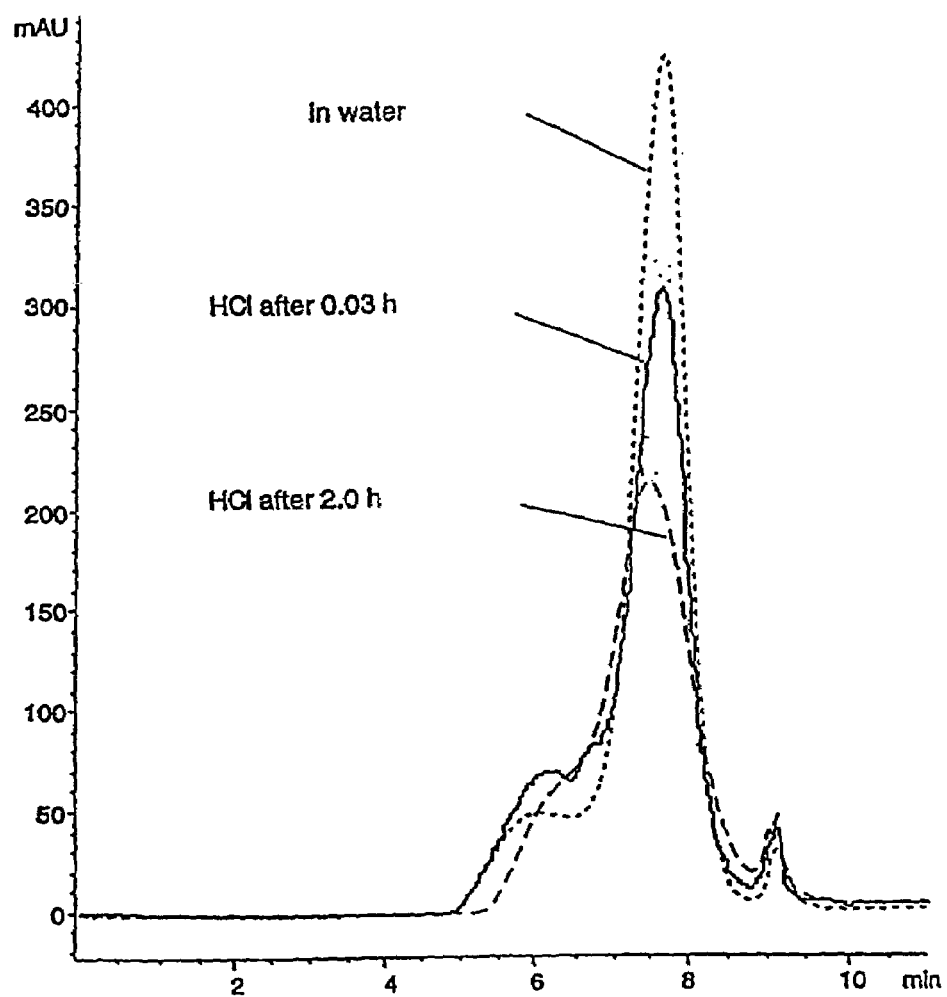

Oooms and Degryse, 1986, "Pathogenesis and Pharmacology of Diarrhea", *Veterinary Research Communications* 10: 355-397.

Pallenbach et al., 1993, "Proanthocyanidins from Quercus petraea Bark", Planta Med. 59: 264-268.

Persinos et al., 1979, "Errors in Chlorothiazide Bioavailability Estimates Based on a Brattton-Marshall Colorimetric Method for Chlorothiazide in Urine", *J. Pharm. Sci.* 68: 124.

Sethi, 1977, "Inhibition of RNA-Directed DNA Polymerase Activity of RNA Tumor Viruses by Taspine", *Canadian J. Pharm. Sci.* 12: 7-9.

Silverstein, 1989, "Procyandin from Black Bean (Phaseolus Vulgars): Effects on Transport of Sodium, Chloride, Glucose, and Alanine in the rat ileum", Washington State University (Dissertation).

Strombeck, 1995, "Diagnosis and Treatment of Chronic Diarrhea", *The Veterinary Quarterly* 17(Suppl. 1): S12-S15.

Tanaka et al., 1992, "Tannins and Related Compounds. CXVI. Six New Complex Tannins, Guajavins, Psidinins and Psiguavin from the Bark of Psidium guajava L.", Chem. Pharm. Bull. 40: 2092-2098.

Toda et al., 1991, "The Protective Activity of Tea Against Infection by Vibrio cholerae 01", J. App. Bact. 70: 109-112.

Ubillas et al., 1994, "SP-303, an Antiviral Oligomeric Proanthocyandin from the Latex of Croton lecheri (Sangre de Drago)", Phytomedicine 1: 77-106.

Vermut, 1994, "Rearing and Management of Diarrhoea in Calves to Weaning", *Australian Veterinary Journal* 71(2): 33-41.

Yoshida et al., 1992, "Tannins and Related Polyphenols of Rosaceous Medicinal PLants. XII. Roshenins A-E, Dimeric Hydrolyzable Tannins from Rosa henryi BOUL.", Chem. Pharm. Bull. 40: 1997-2001.

Yoshida et al., 1993, "Two Polyphenol Glycosides and Tannins from Rosa-Cymosa", *Phytochemistry* 32: 1033.

Craig, 1996, "Shaman Gets Positive Efficacy Data on Diarrhea Drug", *Bioworld Today* 7(164): 1-2.

Foo et al., 1989, "Procyanidin polymers of Douglas Fir bark: structure from degradation with phloroglucinol", *Phytochemistry* 28:3185-3190.

Foo et al., 1986, "Some Recent Advances in the Chemistry Of Condensed Tannins (proanthocyanidin polymers) Relevant To Their Use As Industrial Chemicals", Appita 39:477-480.

Hemingway, 1988, "Reactions At The Interflavanoid Bond Of Proanthocyanidins" in *Proceedings of the North American Tannin Conference. Chemistry and Significance of Condensed Tannins*, Hemingway and Karchesy (eds.), *Plenum Press*, NY, pp. 265-283.

Porter, 1989, *Methods in Plant Biochemistry* 1:389-418.

Porter et al., 1986, "The Conversion Of Procyanidins And Prodelphinidins To Cyanidin And Delphinidin", *Phytochemistry* 25:223-230.

Remington's Pharmaceutical Sciences, 16th Edition, 1980, *Mack Publishing Inc.*, Easton, pp. 87:1530 and 1585-1593.

Thompson et al., 1972, *Plant Proanthocyanidins. Part I. Introduction: the Isolation, Structure, and Distirbution in Nature of Plant Procyanidins* J.C.S. Perkin 1:1387-1399.

Davenport et al., "A Novel Plant-Derived Inhibitor of cAMP-Mediated Cl Secretion" *Pediatric Pulmonology* S13:abstract 34 (Aug. 16, 1996).

The Biologically Active Constituents of "Sangre De Drago" A Traditional South American Drug, 1992.

Black, "The Prophykaxis and Therapy of Secretory Diarrhea", Medical Clinics of North America 56(3): 611-621, date unknown.

Chen et al., "Studies on the Anti-Tumor. Anti-Bacterial, and Woung-Healing Properties of Dragon's Blood", Planta Med. 60: 541-545, date unknown.

* cited by examiner

METHOD OF TREATING SECRETORY DIARRHEA WITH ENTERIC FORMULATIONS OF PROANTHOCYANIDIN POLYMER

This is a continuation of application Ser. No. 09/066,989, filed Apr. 23, 1998, currently abandoned, which is a continuation-in-part of application Ser. No. 08/730,772, filed Oct. 16, 1996, currently abandoned, both of which are incorporated herein by reference in their entireties.

Shaman Pharmaceuticals, Inc. and the University of North Carolina are parties to a joint research agreement.

1. FIELD OF THE INVENTION

The present invention relates to pharmaceutical formulations of proanthocyanidin polymeric compositions which are effective for the treatment of diarrhea. In particular, the invention relates to pharmaceutical formulations of a proanthocyanidin polymeric composition, which has been isolated from a *Croton* spp. or *Calophyllum* spp., which formulations are effective for the treatment of secretory diarrhea, particularly for the reduction of the fluid loss and resulting dehydration associated with secretory diarrheas. A preferred embodiment of the invention relates to pharmaceutical formulations of proanthocyanidin polymeric compositions which protect the compositions from the acid environment of the stomach after oral administration, particularly those formulations which are enteric coated, and formulations of directly compressible proanthocyanidin polymer compositions.

2. BACKGROUND OF THE INVENTION

Citation or identification of any reference in Section 2 or any other section of this application shall not be construed as an admission that such reference is available as prior art for the present invention.

2.1. Secretory Diarrheas

Secretory diarrheas, also called watery diarrheas, are a major source of illness and mortality in developing countries, particularly in infants and young children and also affect a significant proportion of visitors from developed to developing countries and can also affect any person visiting a foreign country (called "traveler's diarrhea"). Secretory diarrhea is characterized by the loss of both fluid and electrolytes through the intestinal tract, leading to serious and often life-threatening dehydration. Secretory diarrhea is caused by a variety of bacterial, viral and protozoal pathogens and also results from other non-infectious etiologies such as ulcerative colitis, inflammatory bowel syndrome, and cancers and neoplasias of the gastrointestinal tract. In fact, it is believed that all types of diarrheal disease may have a secretory component.

Two major bacterial sources of secretory diarrhea are *Vibrio cholerae* and *Escherichia coli*. The enterotoxigenic types of *E. coli* represent an important source of secretory diarrhea in developing countries and are the major cause of traveler's diarrhea. Other strains of *E. coli* which cause diarrhea include enterohemorrhagic, enteroinvasive, and enteropathogenic and other strains. Other bacterial agents which cause secretory diarrhea include other *Vibrio* spp., *Campylobacter* spp., *Salmonella* spp., *Aeromonas* spp., *Plesiomonas* spp., *Shigella* spp., *Klebsiella* spp., *Citrobacter* spp., *Yersinia* spp., *Clostridium* spp., *Bacteriodes* spp., *Staphylococcus* spp., and *Bacillus* spp, as well as other enteric bacteria. Secretory diarrhea can also be caused by protozoal pathogens such as *Cryptosporidium* spp, for example *Cryptosporidium parvum*. See generally, Holland, 1990, *Clin. Microbiol. Rev.* 3:345; Harris, 1988, *Ann. Clin. Lab. Sci.* 18:102; Gracey, 1986, *Clin. in Gastroent.*, 15:21; Ooms and Degryse, 1986, *Veterinary Res. Comm.* 10:355; Black, 1982, *Med. Clin. Nor. Am.*, 66:611.

*V. cholerae*, the enterotoxigenic strains of *E. coli*, and a variety of other enteric bacteria elicit secretory diarrhea via similar mechanisms. These pathogens produce a toxin which binds a specific receptor on the apical membrane of the intestinal epithelium. Binding of the receptor triggers an adenylate cyclase- or guanylate cyclase-mediated signal transduction leading to an increase in cAMP or cGMP. This regulatory cascade, apparently acting through phosphorylation of specific apical membrane proteins, stimulates chloride efflux into the gut from the intestinal epithelial crypt cells and inhibits normal resorption of sodium and chloride ions by the intestinal epithelial villus cells. The increased chloride and sodium ion concentration osmotically draws water into the intestinal lumen, resulting in both dehydration and loss of electrolytes. Agents which reduce chloride ion secretion will, therefore, prevent the fluid movement into the intestine and resulting net fluid elimination. Thus, such agents are particularly useful for treating and preventing the dangerous dehydration and electrolyte loss associated with secretory diarrhea.

The pharmaceutical compositions of the present invention are particularly useful for treatment of traveler's diarrhea and non-specific diarrhea. Traveler's diarrhea, which is a type of secretory diarrhea, is defined as diarrhea experienced by citizens of industrialized nations who travel to "third world" countries. An example of traveler's diarrhea is diarrheal disease experienced by United States citizens that travel to Mexico for the first time and have diarrhea within the 3-5 days of arrival (Castelli & Carose, 1995, *Chemotherapy* 4(supp. 1): 20-32). Bacteria are estimated to be responsible for 85% of traveler's diarrhea with enterotoxigenic *Escherichia coli* (ETEC), *Shigella* spp., and *Campylobacter jejuni* being the principal etiologic agents. Protozoa and viruses also cause traveler's diarrhea but at lower frequencies than bacteria (DuPont, 1995, *Chemotherapy* 4(supp. 1):33-39). In Mexico, in the summer months (May to November), the predominant etiologic agent associated with traveler's diarrhea is ETEC, whereas in the winter months, the principal organism is *Campylobacter jejuni* (DuPont, 1995, "Traveler's diarrhea", M. Blaser et al., eds., pp. 299-311, Raven Press, New York). Approximately 40% of first time United States travelers to Mexico experience traveler's diarrhea.

In contrast to traveler's diarrhea, non-specific diarrhea (NSD), which also appears to have a secretory component, is an acute endemic diarrheal disease experienced by indigenous populations. The attack rate of non-specific diarrhea in Mexican residents is 7% (H.L. DuPont, personal communication). Unlike traveler's diarrhea, however, non-specific diarrhea generally does not respond to antibiotic therapy and the etiology is not known.

Since 1975, DuPont and colleagues at the University of Texas Health Sciences Center at Houston have conducted a series of clinical trials in Mexico to study the efficacy of a variety of antidiarrheal drugs. Based on the results of the placebo groups from these studies, they have been able to characterize the natural history of traveler's diarrhea and non-specific diarrhea in United States travelers and Mexican nationals, respectively. The data show clear differences in both the intensity and duration of diarrheal disease between patients who have traveler's diarrhea in the summer and patients with non-specific diarrhea. In 5 day evaluations, the duration of disease (mean time to last unformed stool from time of enrollment) was 69 hours for United States travelers compared to 38 hours for Mexican nationals (p=0.0001). If the total number of stools passed since the time of enrollment is analyzed (0-120 hours), travelers from the United States have 10.6 stools versus 5.6 stools for Mexican residents (p=0.0001) (H.L. DuPont, personal communication).

Although not as much data is available on traveler's diarrhea occurring in the winter months in Mexico, in general the diarrheal disease in new arrivals from the United States is similar to diarrhea experienced by United States residents who have been in Mexico for several months. It tends to be less severe than traveler's diarrhea in the summer, and more severe than non-specific diarrhea (H.L. DuPont, personal communication).

Secretory diarrheas are also associated with viral infections, such as, diarrheas which accompany Human Immunodeficiency Virus (HIV) infection and Acquired Immuno Deficiency Syndrome (AIDS), and rotavirus infection, in particular. Almost all AIDS patients suffer from diarrhea at some point during the course of the disease, and 30% of AIDS patients suffer from chronic diarrhea. The diarrhea that accompanies AIDS has been termed "HIV-Associated Chronic Diarrhea." This diarrheal component of HIV disease is thought to be caused, at least in some patients, by a secondary infection of protozoal pathogens, particularly *Cryptosporidium* spp. Additionally, rotavirus infection is a substantial cause of diarrhea particularly in infants and young children in developing countries.

Secretory diarrhea is also a significant problem in non-human animals, particularly in farm animals, such as bovine animals, swine, sheep (ovine animals), poultry (such as chickens), and equine animals, and other domesticated animals such as canine animals and feline animals. Diarrheal disease is particularly common in young and recently weaned farm animals. Diarrheal disease in farm animals, particularly food animals such as cattle, sheep and swine, is often caused by bacterial pathogens such as enterotoxigenic, enterohemorrhagic and other *E. coli*, *Salmonella* spp., *Clostridium perfringens*, *Bacteriodes fragilis*, *Campylobacter* spp., and *Yersinia enterocolitica*. Additionally, protozoal pathogens, particularly *Cryptosporidium parvum*, and viral agents, particularly rotaviruses and coronaviruses, are significant causes of diarrhea in farm animals. Other viral agents which have been implicated in diarrhea of farm animals include togavirus, parvovirus, calicivirus, adenoviruses, bredaviruses, and astroviruses. See generally Holland, 1990, *Clin. Microbiology Rev.* 3:345; see also Gutzwiller and Blum, 1996, *AJVR* 57:560; Strombeck, 1995, *Veterinary Quarterly* 17(Suppl. 1):S12; Vermunt, 1994, *Austral. Veterinary J.* 71:33; Driesen et al., 1993, *Austral. Veterinary J.* 70:259; Mouricout, 1991, *Eur. J. Epidemiol.* 7:588; Ooms and Degryse, 1986, *Veterinary Res. Comm.* 10:355.

2.2. Plant Extracts Containing Tannins or Proanthocyanidins and Use Against Diarrhea Tannins are found in a wide variety of plants and are classified as either hydrolyzable or condensed. Proanthocyanidins are a group of condensed tannins and are described further below. Many plants used in traditional medicine as treatment or prophylaxis for diarrhea have been found to contain tannins and proanthocyanidins in particular (see, e.g., Yoshida et al., 1993, *Phytochemistry* 32:1033; Yoshida et al., 1992, *Chem. Pharm. Bull.*, 40:1997; Tamaka et al., 1992, *Chem. Pharm. Bull.* 40:2092). Crude extracts from medicinal plants, for example, *Pycanthus angolenis* and *Baphia nitida*, have been shown to have antidiarrheal qualities in animal tests (Onwukaeme and Anuforo, 1993, *Discovery and Innovation*, 5:317; Onwukaeme and Lot, 1991, *Phytotherapy Res.*, 5:254). Crude extracts which contain tannins, in particular extracts from carob pods and sweet chestnut wood, have been proposed as treatments or prophylactics for diarrhea (U.S. Pat. No. 5,043,160; European Patent No. 481,396).

Crude plant extracts containing proanthocyanidins have also been proposed as treatments or prophylactics for diarrhea. For example, crude fruit skin extracts, which contain anthocyanidins as well as other compounds, have been suggested for use against diarrhea (U.S. Pat. No. 4,857,327). The bark from the *Q. petrea* tree, traditionally used against diarrhea, has been shown to contain oligomeric proanthocyanidins (Konig and Scholz, 1994, *J. Nat. Prod.*, 57:1411; Pallenbach, 1993, *Planta Med.*, 59:264). A fraction of *Sclerocarya birrea* bark extract, which also contains procyanidins, reduced the intestinal contractions associated with experimentally-induced diarrhea (Galvez et al., 1993, *Phyt. Res.*, 7:25; Galvez et al., 1991, *Phyt. Res.*, 5:276). However, none of these studies demonstrate that the proanthocyanidins are specifically responsible for the antidiarrheal activity of the extracts.

Other studies suggest that certain preparations containing proanthocyanidins may interfere with cholera toxin action in the gut. Crude tea extract, which contains catechins (proanthocyanidin monomers), has been demonstrated to prevent both cholera toxin-induced morphological changes in cultured CHO cells and cholera toxin-induced intestinal fluid accumulation in mice when administered five minutes after the cholera toxin (Toda et al., 1991, *J. App. Bact.*, 70:109). However, the crude tea extract could not prevent the fluid accumulation in the mouse intestine when administered thirty minutes after the cholera toxin, and the catechins were not shown to be the active agent in the extract. Furthermore, a fraction of *Guazuma ulmifolia* bark extract containing proanthocyanidins reduced cholera toxin-induced ion efflux in isolated rabbit intestinal tissue, apparently through a physical interaction of the polymeric proanthocyanidins with the cholera toxin as determined by SDS-PAGE analysis (Hor et al., 1996, *Phytochemistry* 42:109; Hor et al., 1995, *Planta Med.*, 61:208). Addition of the fraction after addition of the cholera toxin, however, had no effect on chloride ion secretion. Thus, completely contrary to the present invention, this fraction would not be effective to reduce or prevent the fluid loss after exposure to the agent causing the secretory diarrhea and therefore would not be useful as a therapeutic for secretory diarrhea.

Proanthocyanidins have different physiological effects, depending on their structure and source. Other proanthocyanidins are actually contraindicated for treatment or prevention of diarrhea. Oligomeric proanthocyanidins isolated from black bean were shown to increase chloride secretion and reduce sodium resorption in isolated intestinal tissue [Silverstein, 1989, "Procyanidin from Black Bean (*Phaseolus Vulgaris*): Effects on Transport of Sodium, Chloride, Glucose, and Alanine in the Rat Ileum," Washington State University (Dissertation)]. The increased ion concentration in the intestine would thus promote fluid accumulation in the intestinal lumen and aggravate the fluid and electrolyte loss and dehydration associated with secretory diarrhea. In fact, the reference specifically teaches away from the use of proanthocyanidins as a treatment for diarrhea and suggests that the proanthocyanidins might cause secretory diarrhea.

2.3. Proanthocyanidins

Proanthocyanidin and proanthocyanidin polymers are phenolic substances found in a wide variety of plants, particularly those with a woody habit of growth (e.g., *Croton* spp. and *Calophyllum* spp.). The general chemical structure of a polymeric proanthocyanidin consists of linear chains of 5, 7, 3', 4' tetrahydroxy or 5, 7, 3', 5' pentahydroxy flavonoid 3-ol units linked together through common C(4)-(6) and/or C(4)-C(8) bonds, as shown below.

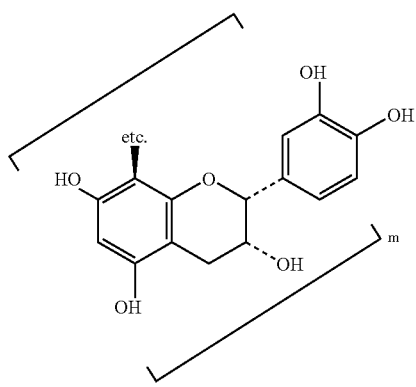

Biosynthetic studies have indicated that proanthocyanidin polymers consist of monomer units of the type shown below. See Fletcher et al., 1977, *J.C.S. Perkin*, 1:1628.

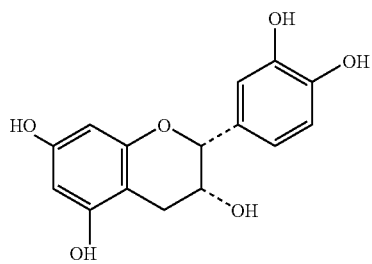

1a R = H
1b R = OH

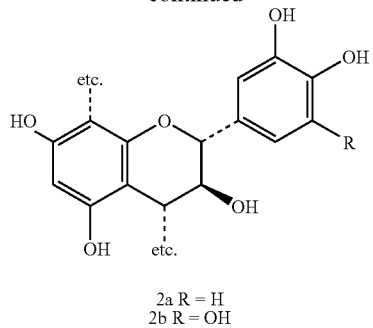

2a R = H
2b R = OH

The monomer unit (generally termed "leucoanthocyanidin") of the polymer chain may be based on either of two stereochemistries of the C-ring, at a 2 and/or 4 position designated cis (called epicatechins) or trans (called catechin). Therefore, the polymer chains are based on different structural units, which create a wide variation of polymeric proanthocyanidins and a large number of possible isomers (Hemingway et al., 1982, *J.C.S. Perkin*, 1:1217). $^{13}$C NMR has been useful to identify the structures of polymeric proanthocyanidins and recent work has elucidated the chemistry of di-, tri- and tetra-meric proanthocyanidins Larger polymers of the flavonoid 3-ol units are predominant in most plants, and are found with average molecular weights above 2,000 daltons, containing 6 or more units (Newman et al., 1987, *Mag. Res. Chem.*, 25:118).

2.4. Ethnobotanical Uses of Extracts and Compounds from *Croton* and *Calophyllum* Species A number of different *Croton* tree species, including *Croton sakutaris, Croton gossypifolius, Croton palanostima, Croton lechleri, Croton erythrochilus* and *Croton draconoides*, found in South America, produce a red viscous latex sap called Sangre de Drago or "Dragon's Blood". Sangre de Drago is most often utilized by mixed descent and native people of the Peruvian Amazon for flu and diarrhea. It is taken internally for tonsillitis, throat infections, tuberculosis, peptic ulcers, intestinal disorders, rheumatism and to enhance fertility and is used by both adults and children. It is also used extensively to stop bleeding, for herpes virus lesions, and for wound healing. The sap is placed directly on open wounds as an anti-infective and to accelerate the healing process. It is also utilized as a vaginal wash in cases of excessive bleeding.

It has been shown that Sangre de Drago from *Croton draconoides* and from *Croton lechleri* contains an alkaloid identified as taspine, which exhibits anti-inflammatory activity (Persinos et al., 1979, *J. Pharm. Sci.*, 68:124). Taspine has also been shown to inhibit RNA-directed DNA polymerase activity in the avian myeloblastosis virus, Rauscher leukemia virus and Simian sarcoma virus (Sethi, 1977, *Canadian J. Pharm. Sci.*, 12:7).

A variety of phenolic and diterpene compounds isolated from Sangre de Drago were tested for their antitumor, antibacterial and wound healing properties (Chen et al., *Planta Med.*, 60:541). The proanthocyanidins in the sap were found to have little antitumor or antibacterial activity and slight wound healing activity.

U.S. Pat. No. 5,211,944 first described the isolation of an aqueous soluble proanthocyanidin polymer composition from *Croton* spp. and the use of the composition as an antiviral agent (See also Ubillas et al., 1994, *Phytomedicine*, 1:77). The proanthocyanidin polymer composition was shown to have antiviral activity against a variety of viruses including, respiratory syncytial, influenza, parainfluenza and herpes viruses.

*Calophyllum inophylum* is a tree ranging from India to East Africa to Polynesia. Seed oil is used in folk medicine as an antiparasitic in treatment of scabies, ringworm and dermatosis as well as other uses such as analgesia. In Indo-China, the powdered resin is used for ulcers and wound healing. In Indonesia, the bark is applied externally to treat swollen glands and internally as a diuretic. The sap is used as an emollient for chest pain as well as for tumors and swelling. Leaf extracts are used as a wash for inflamed eyes. The Cambodians use leaf extracts in inhalations for treatment of vertigo and migraine. The Samoans use the sap as an arrow poison.

U.S. Pat. No. 5,211,944 also discloses the isolation of an aqueous soluble proanthocyanidin polymer composition from *Calophyllum inophylum* and the use of this composition as an antiviral agent.

It has been determined that the proanthocyanidin polymer compositions of the invention are acid labile and subject to inactivation by the acidic environment of the stomach. Before the present application, no disclosure has been made of a pharmaceutical composition of a proanthocyanidin polymer composition isolated from either *Croton* spp. or *Calophyllum* spp. which protects the proanthocyanidin polymer composition from the acidity of gastric fluid so that the proanthocyanidin polymer composition can be administered orally for treatment of secretory diarrhea.

The need remains for an effective pharmaceutical composition, the administration of which will reduce the ion efflux into the gut elicited by secretory diarrhea. Such an agent would be useful to prevent the fluid and electrolyte loss and dehydration caused by secretory diarrhea. The object of the present invention is to provide an effective pharmaceutical formulation of an antidiarrheal agent which will fulfill this need, and specifically to provide a pharmaceutical formulation which will protect the antidiarrheal agent from the acidity of the stomach as well as methods for treating diarrhea using the pharmaceutical formulation.

3. SUMMARY OF THE INVENTION

The present invention relates to pharmaceutical compositions comprising a therapeutically effective amount of an antidiarrheal agent comprising a proanthocyanidin polymer composition. The proanthocyanidin polymer composition is preferably prepared from a *Croton* spp, preferably *Croton lechleri*. The proanthocyanidin polymer composition can also be prepared from a *Calophyllum* spp., in particular *Calophyllum inophylum*.

The pharmaceutical compositions of the invention are formulated to protect the proanthocyanidin polymeric composition from degradation by the acidic conditions of the stomach and from interactions with proteins, such as pepsin, present in the stomach. In a preferred embodiment, the proanthocyanidin polymer composition is enteric coated. In a more preferred embodiment, the pharmaceutical composition contains a proanthocyanidin polymer composition that can be directly compressed into a tablet. As used herein "directly compressible" means that a proanthocyanidin polymer composition, in the absence of any excipients, additives, diluents, etc., that improve compressibility, can be directly pressed into a tablet having a pharmaceutically suitable hardness, i.e., a hardness (also referred to as "crushing strength") greater than 6 kp, and friability, i.e., a friability of no more than 1% loss in weight. Preferably, the directly compressible proanthocyanidin polymer composition is directly compressed (optionally in the presence of a lubricant such as, but not limited to, magnesium stearate) into a tablet of pharmaceutically suitable hardness and friability, and is subsequently enterically coated.

Whether a proanthocyanidin polymer composition can be directly compressed into a tablet of pharmaceutically acceptable hardness and friability can be determined by any method known in the art, for example by compressing a formulation into a tablet and determining its hardness and friability by known methods, e.g., as described in Sections 5.1 and 10, infra. To be pharmaceutically acceptable, a tablet has a hardness greater than 6 kp (but preferably a hardness of 8-14 kp, more preferably 10-13 kp) and a friability of not more than 1% loss in weight (but preferably a friability of not more than 0.8% loss in weight, and more preferably a friability of not more than 0.5% loss in weight).

In another preferred embodiment, the proanthocyanidin polymer composition is provided in combination with a substance able to reduce the secretion of stomach acid or able to reduce the acidity of stomach fluid.

The present invention also encompasses methods for treating diarrhea, particularly secretory diarrhea, in warm blooded animals, including humans, comprising administering, to a non-human animal or human suffering from diarrhea, a pharmaceutical composition comprising a therapeutically effective amount of a proanthocyanidin polymer composition isolated from a *Croton* spp., or a *Calophyllum* spp., or a pharmaceutically acceptable derivative thereof, formulated to protect the proanthocyanidin polymer composition from the stomach environment, e.g., from the action of stomach acid and interaction with proteins, such as pepsin, in the stomach and a pharmaceutically acceptable carrier. In addition, the present invention encompasses methods for treating secretory diarrhea in animals, including humans, comprising administering, to a non-human animal or human suffering from diarrhea, (a) a pharmaceutical composition comprising a therapeutically effective amount of a proanthocyanidin polymer composition isolated from a *Croton* spp., or a *Calophyllum* spp., or a pharmaceutically acceptable derivative thereof, and a pharmaceutically acceptable carrier; and (b) a pharmaceutical composition either comprising an amount effective to inhibit stomach acid secretion of a compound that is effective to inhibit stomach acid secretion or comprising an amount effective to neutralize stomach acid of a compound that is effective to neutralize stomach acid, and a pharmaceutically acceptable carrier.

The present invention also provides methods for preventing diarrhea in warm blooded animals, including humans, comprising administering, to a non-human animal or human at risk of developing diarrhea, a pharmaceutical composition comprising a prophylactically effective amount of a proanthocyanidin polymer composition isolated from a *Croton* spp., or a *Calophyllum* spp., or a pharmaceutically acceptable derivative thereof, formulated to protect the proanthocyanidin polymer composition from the stomach environment, and a pharmaceutically acceptable carrier.

The present invention further relates to methods of producing a proanthocyanidin polymer composition that can be directly compressed, i.e. compressed without any excipients, into a tablet of pharmaceutically acceptable hardness and friability. In a preferred embodiment, the method of producing a proanthocyanidin polymer composition that can be directly compressed into a tablet comprises (1) extracting an aqueous solution of the latex from a *Croton* spp. with a short chain alcohol, preferably n-butanol; (2) concentrating the aqueous phase of the extracted material by ultrafiltration; (3) chromatographing the retentate from the ultrafiltration step on a cation exchange column, preferably a CM-Sepharose column; (4) fractionating the material from the cation exchange column on a size exclusion column, preferably an LH-20 column; and (5) pooling the fractions collected from the size exclusion column that contain material with detectable absorbance at 460 nm. The invention also includes pharmaceutical compositions comprising the product of the process for producing a proanthocyanidin polymer composition that can be directly compressed into a tablet of pharmaceutically acceptable hardness and friability and methods of treating and preventing diarrhea in a human or non-human animal by administering a pharmaceutical composition containing the directly compressible proanthocyanidin polymer composition.

4. BRIEF DESCRIPTION OF THE FIGURES

FIG. 1. An overlay of HPLC chromatograms showing the chromatographic profiles of the proanthocyanidin polymer composition from *C. lechleri* after different treatments as UV absorption in milliabsorption units (mAU) over time of chromatography in minutes. The chromatogram graphed as a dotted line depicts the profile of the proanthocyanidin polymer composition after incubation in water ("in water"), the solid line depicts the proanthocyanidin polymer composition profile after incubation in HCl for 0.03 hours ("HCl after 0.03 h"), and the dashed line depicts the proanthocyanidin polymer composition from *C. lechleri* profile after incubation in HCl for 2.0 hours ("HCl after 2.0 h").

Figure 2:
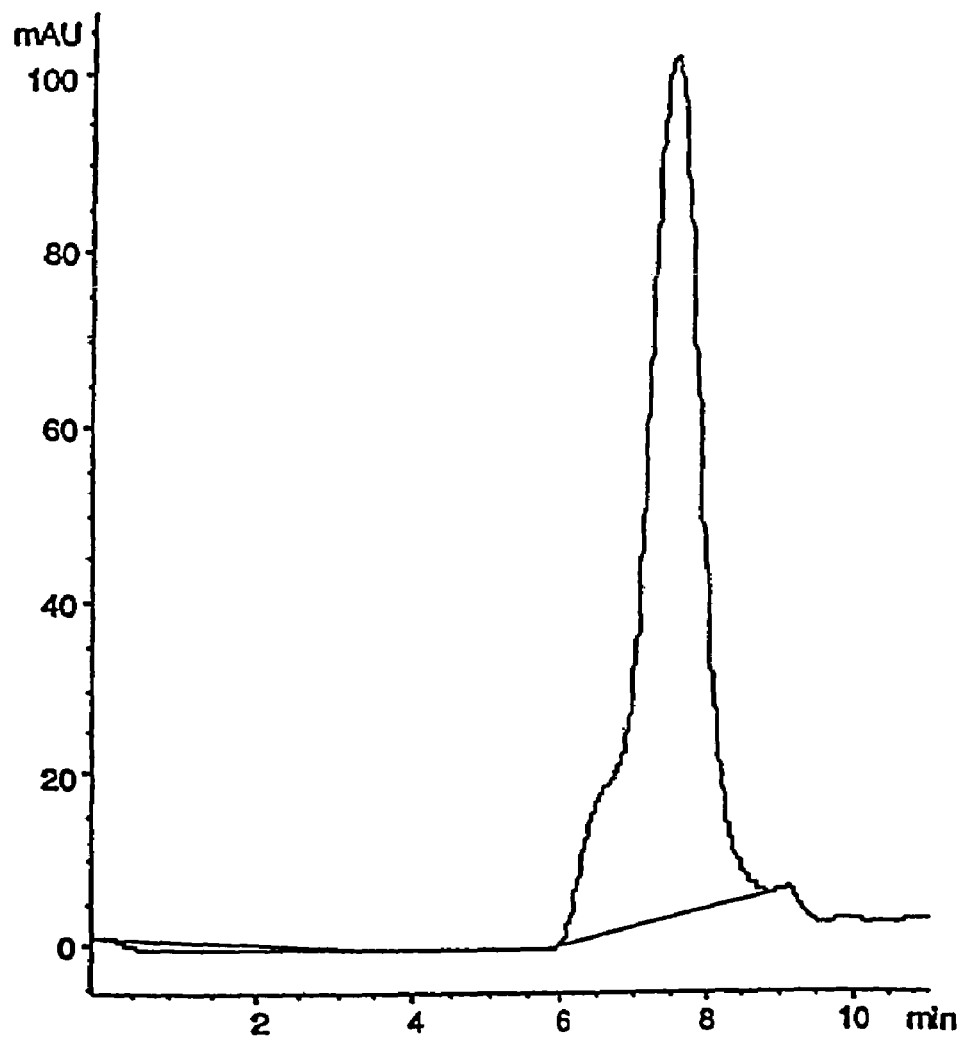

FIG. 2. A sample HPLC chromatogram of the proanthocyanidin polymer composition from *C. lechleri* after incubation in simulated gastric fluid at 37° C. for 0.03 hours. The chromatogram is graphed as UV absorption (mAU) over time in minutes.

Figure 3:
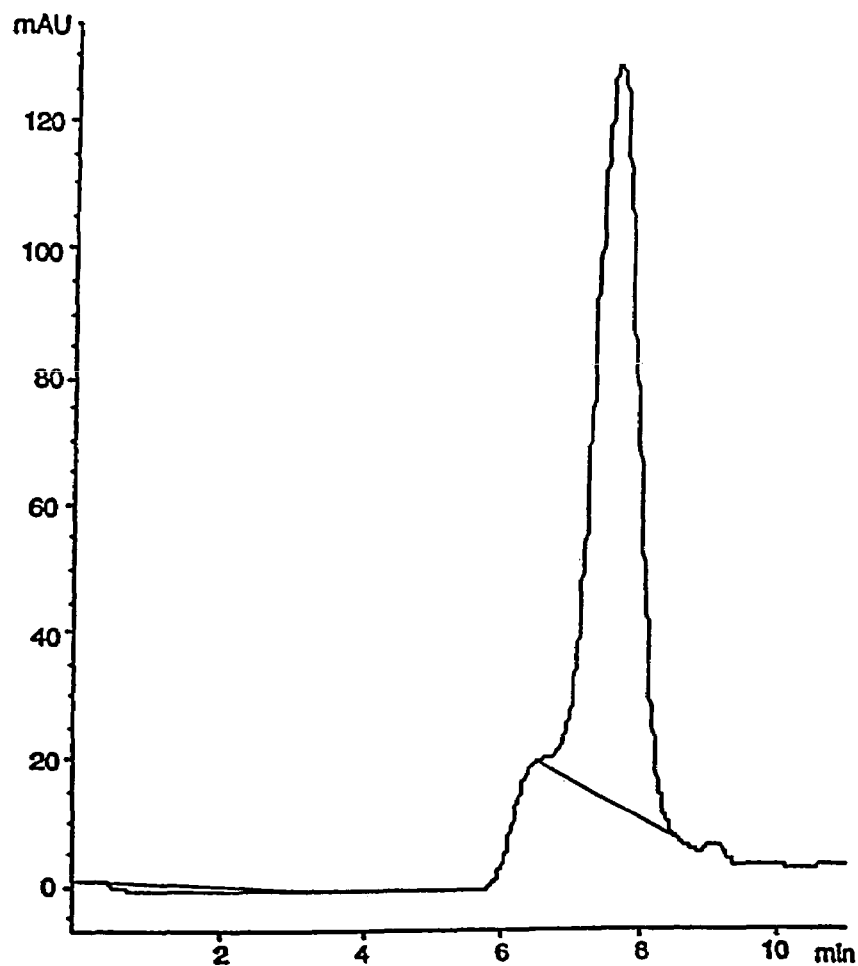

FIG. 3. A sample HPLC chromatogram of the proanthocyanidin polymer composition from *C. lechleri* after incubation in simulated gastric fluid at 37° C. for 2 hours. The chromatogram is graphed as UV absorption (mAU) over time in minutes.

Figure 4:
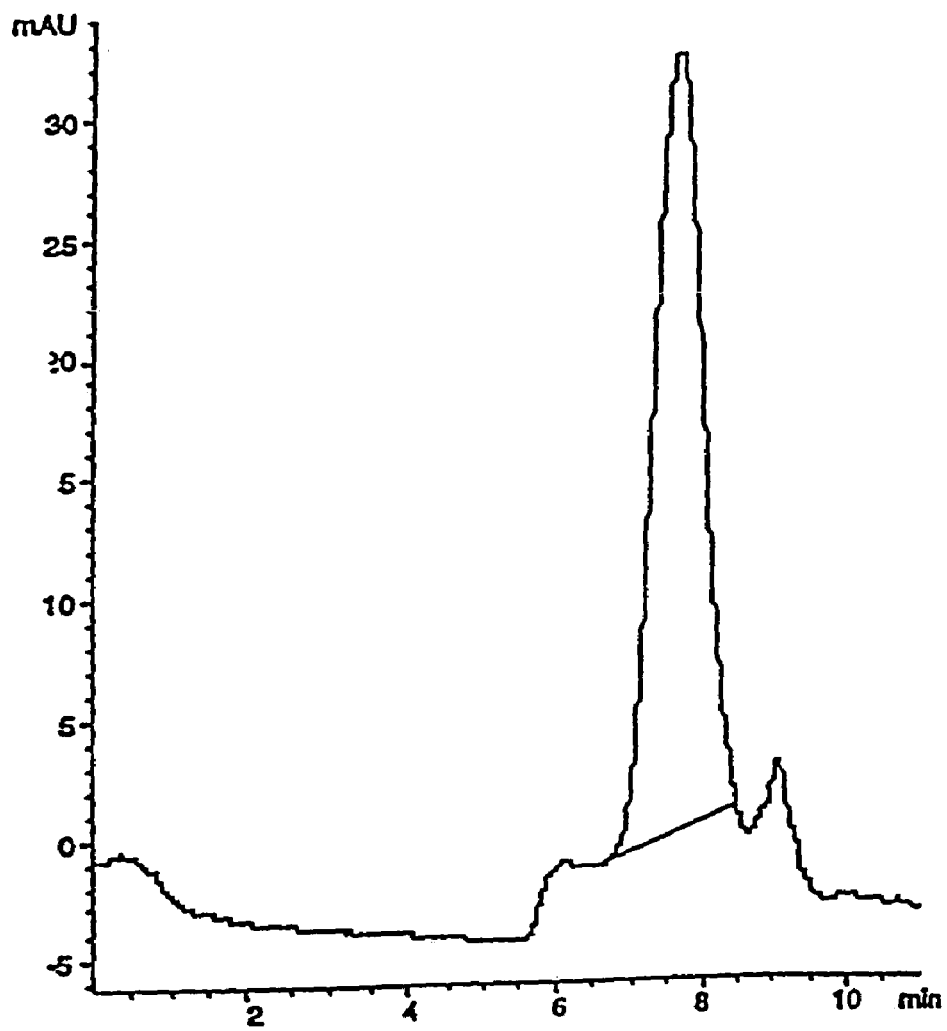

FIG. 4. A sample HPLC chromatogram of the proanthocyanidin polymer composition from *C. lechleri* after incubation in simulated gastric fluid at 37° C. for 2 hours, and followed by incubation for 4 more hours after dilution 1:1 in simulated intestinal fluid. The chromatogram is graphed as UV absorption (mAU) over time in minutes.

Figure 5:
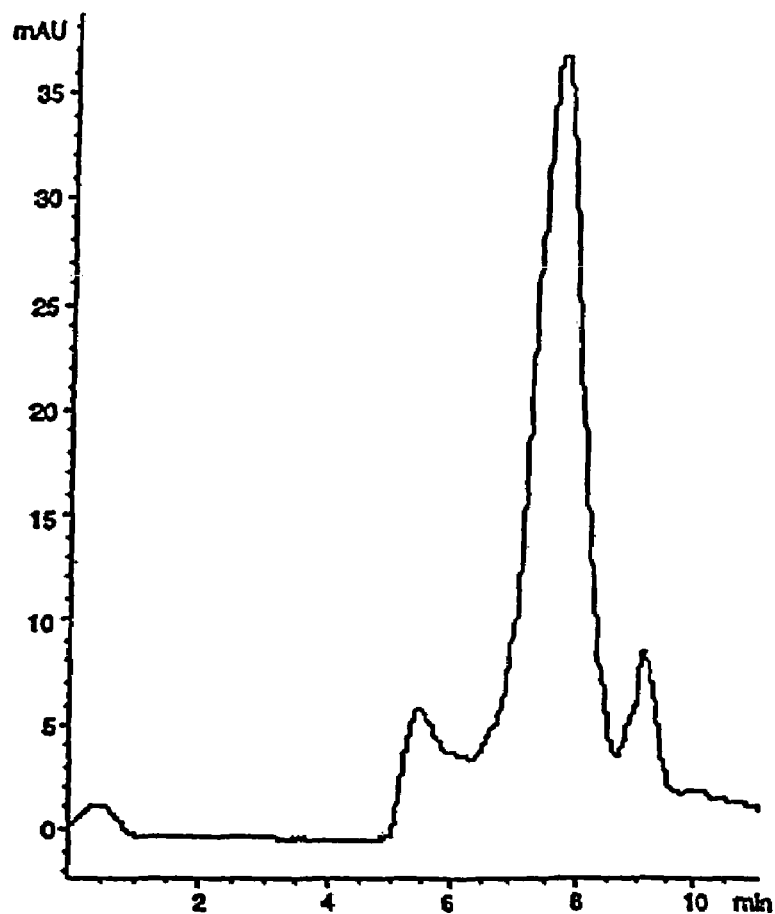

FIG. 5. A sample HPLC chromatogram of the proanthocyanidin polymer composition from *C. lechleri* after incubation in simulated gastric fluid at 37° C. for 2 hours, and followed by incubation for 6 more hours after dilution 1:1 in simulated intestinal fluid. The chromatogram is graphed as UV absorption (mAU) over time in minutes.

Figure 6:
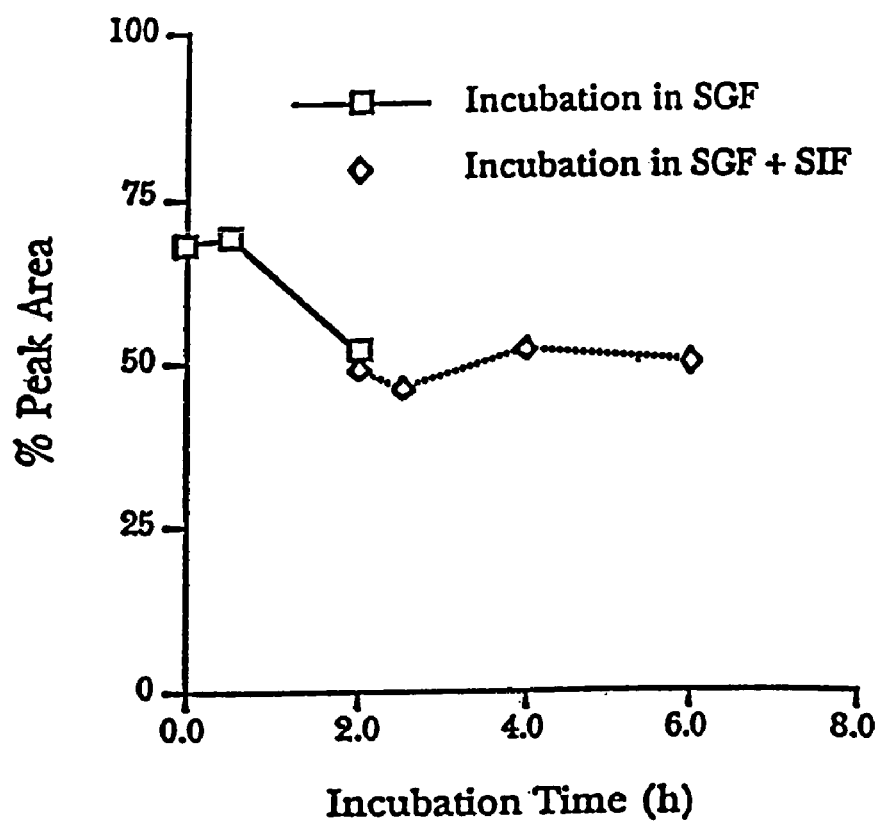

FIG. 6. Plot of the percentage of peak area ("% Peak Area"), as calculated by dividing peak area of the HPLC profile of the proanthocyanidin polymer composition from *C. lechleri* in the test-medium by the peak area of the HPLC profile of the proanthocyanidin polymer composition in water and multiplying by 100, as a function of incubation time in hours. The line with open squares represents the % peak area of the proanthocyanidin polymer composition after incubation in SGF (simulated gastric fluid). The dotted line with diamonds represents the % peak area of the proanthocyanidin polymer composition after 2 hours of incubation in SGF and then dilution 1:1 into SIF (simulated intestinal fluid) for further incubation.

Figure 7:
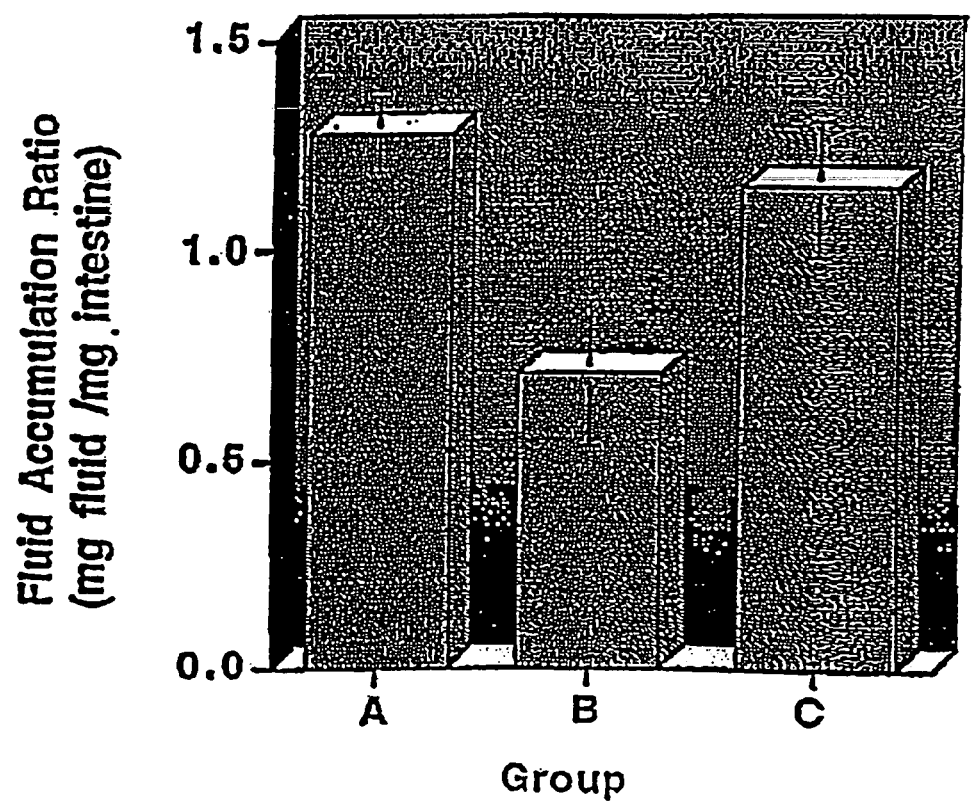

FIG. 7. This bar graph depicts the effect of the enteric coated formulation of the proanthocyanidin polymer composition from *C. lechleri* on intestinal fluid accumulation in mice exposed to cholera toxin. Results are presented as an average, for each group of mice A-C, of the fluid accumulation ratio in mg fluid/mg intestine. Mice in group A were treated only with water; mice in group B were treated with 131 mg enteric coated proanthocyanidin polymer composition in guar gum/kg; mice in group C were administered "EUDRAGIT™" and sugar with guar gum. The mice in all groups were evaluated at 7 hours after exposure to the cholera toxin. See Section 7, infra for details.

Figure 8:
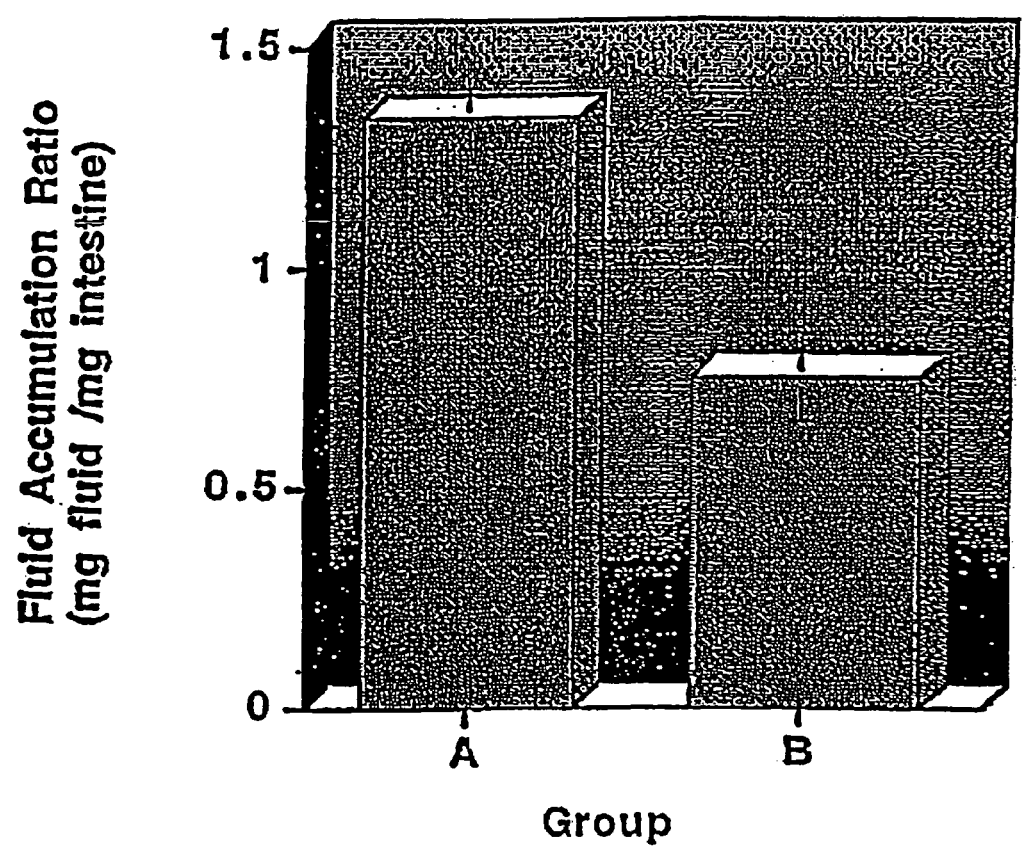

FIG. 8. This bar graph depicts the effect of the enteric coated formulation of the proanthocyanidin polymer composition from *C. lechleri* on intestinal fluid accumulation in mice exposed to cholera toxin. Results are presented as an average, for groups of mice A and B, of the fluid accumulation ratio in mg fluid/mg intestine. Mice in group A were treated with "EUDRAGIT™" and sugar in water, and mice in group B were treated with 131 mg enteric coated proanthocyanidin polymer composition/kg.

Figure 9:
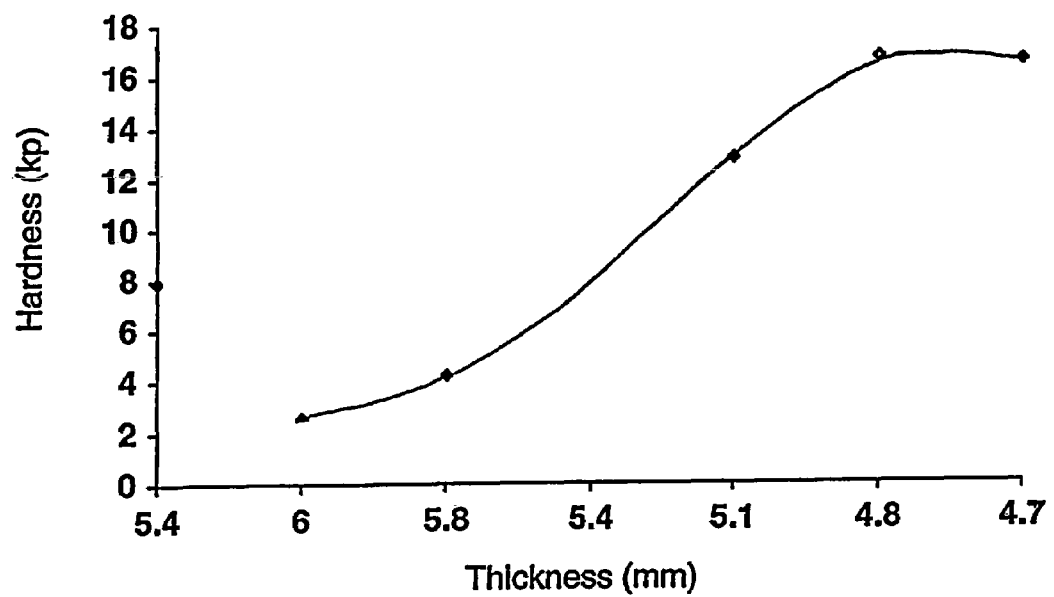

FIG. 9. This graph depicts the hardness (in kp) of 250 mg of the proanthocyanidin polymer composition compressed into tablets of varying thicknesses (in mm).

5. DETAILED DESCRIPTION OF THE INVENTION

5.1. Preparation of the Proanthocyanidin Polymer Composition

The proanthocyanidin polymer composition, effective for treatment of diarrhea, is comprised of monomeric units of leucoanthocyanidins. Leucoanthocyanidins are generally monomeric flavonoids which include catechins, epicatechins, gallocatechins, galloepicatechins, flavanols, flavonols, and flavan-3,4-diols, leucocyanidins and anthocyanidins. The proanthocyanidin polymer composition useful for treating secretory diarrhea is comprised of polymers of 2 to 30 flavonoid units, preferably 2 to 15 flavonoid units, more preferably 2 to 11 flavonoid units and most preferably an average of 7 to 8 flavonoid units with a number average molecular weight of approximately 2500 Mn. The proanthocyanidin polymer composition is preferably soluble in an aqueous solution.

The proanthocyanidin polymer composition used in the present invention is preferably isolated from a *Croton* spp. or *Calophyllum* spp by any method known in the art. For example, the proanthocyanidin polymer composition may be isolated from a *Croton* spp. or *Calophylum* spp. by the method disclosed in U.S. Pat. No. 5,211,944 or in Ubillas et al. (1994, *Phytomedicine* 1: 77-106), both of which are incorporated herein by reference.

In a preferred embodiment, the proanthocyanidin polymer composition is directly compressed, that is, the proanthocyanidin polymer composition, without any excipients, can be compressed into a tablet, or other pharmaceutical formulation, that has a pharmaceutically acceptable hardness and friability. Whether a particular proanthocyanidin polymer composition is directly compressible can be determined by any method known in the art for determining the compressibility of a pharmaceutical substance (see, e.g., Modern Pharmaceuticals, Second Edition, Banker, G. S, and Rhodes, C. T. eds. (Marcel Dekker, Inc., New York (1990), pp. 417-419)). By way of example but not by way of limitation, compressibility may be determined by compressing a set amount of the proanthocyanidin polymer composition to be tested in a normal tableting machine, wherein sets of tablets are formed under increasing amounts in pressure. The greater the compression pressure, the thinner and harder the tablet will be. The hardness of the sets of tablets is then determined by a conventional hardness tester, which measures the amount of force just necessary to fracture the tablet. The hardness of the tablet formed will increase with the amount of pressure used to make the tablet, until the substance reaches the maximum hardness to which it can be compressed. Tablets compressed beyond this maximum point will not increase in hardness.

Preferably, the directly compressible proanthocyanidin polymer composition can be compressed into tablets having a hardness of greater than 6 kp (kiloponds), preferably a hardness of 8 to 14 kp, more preferably a hardness of 10 to 13 kp.

The ability for a proanthocyanidin polymer composition to be directly compressed can also be determined by measuring the friability of tablets formed from the proanthocyanidin polymer composition. The friability can be determined by conventional methods known in the art, such as the USP friability test (see USP 23, Tablet Friability <1216>). A directly compressible proanthocyanidin polymer composition can be compressed into a tablet that has a friability of not more than 1% loss in weight, preferably less than 0.8% loss in weight, more preferably less than 0.5% loss in weight.

In a preferred embodiment, the directly compressible proanthocyanidin polymer composition is isolated by the method described below:

Latex collected from *Croton lechleri* plants is mixed with purified water (preferably one part latex to two parts purified water) and then any insoluble material in the latex solution is allowed to settle, e.g., by leaving the mixture at 4° C. overnight (12 hours). The supernatant is pumped away from the residue and then extracted with a short chain alcohol, such as n-butanol, and preferably is extracted multiple times, more preferably three times. After each extraction, the alcohol phase is discarded and the aqueous phase retained. The aqueous phase is concentrated, for example, using an ultrafiltration device with a 1 kD cut-off membrane. This membrane can be a low protein binding cellulose membrane, or, alternatively, a polypropylene, teflon or nylon membrane can be used. The membrane used should be compatible with acetone. The purpose of the ultrafiltration is to remove the water from the material. The retentate from the ultrafiltration is then concentrated to dryness, for example using tray-dryers at approximately 37° C. (±2° C.).

The dried material is subsequently dissolved in water and then chromatographed on a cation exchange column (for example, a CM-Sepharose column) and a size exclusion column (for example, an LH-20 column). In the preferred two column system, material is run over a CM-Sepharose and then an LH-20 column in a series. Specifically, the dissolved material is loaded onto the cation exchange column and then washed with purified water. The proanthocyanidin polymer material is eluted from the cation exchange column with an aqueous acetone solution (preferably 30% acetone), thereby loading the proanthocyanidin polymer material onto the sizing column. The sizing column is disconnected from the cation exchange column and the material is then eluted off of the sizing column with an aqueous acetone solution (preferably 45% acetone). The fractions are collected and monitored with a UV detector, e.g., at a wavelength of 460 nm. Fractions containing the proanthocyanidin polymer material are combined and concentrated, for example, by ultrafiltration using, e.g., a 1 kD cut-off membrane (as described above for the ultrafiltration step prior to the chromatography steps). The retentate may then be concentrated to dryness using a suitable drying method, such as but not limited to a rotary evaporator, at a temperature of approximately 37° C. (±2° C.). Other suitable drying methodologies include, but are not limited to, tray drying and spray drying.

In a specific embodiment, the directly compressible proanthocyanidin polymer composition is isolated as described in Section 10, infra.

In a preferred embodiment, the proanthocyanidin polymer composition is isolated from *Croton lechleri*. In another embodiment, the proanthocyanidin polymer composition is isolated from *Calophyllum inophylum*.

5.2. Pharmaceutical Formulations

The present invention is based upon the discovery that the proanthocyanidin polymer composition is labile in the environment of the stomach and is stable at pH 5.0 to approximately pH 8.0 (see Section 6, infra). Accordingly, the invention provides pharmaceutical formulations of proanthocyanidin polymer compositions which protect the compositions from the acidity and enzymatic action of gastric secretions. In a preferred embodiment, the pharmaceutical formulations of the invention contain the proanthocyanidin polymer composition with an enteric coating along with another pharmaceutically acceptable vehicle. In a more preferred embodiment, a directly compressible proanthocyanidin polymer composition (i.e, that can be directly compressed, without excipients, into a tablet of pharmaceutically acceptable hardness and friability) compressed into a tablet, optionally with a lubricant, such as but not limited to magnesium stearate, and enteric coated. In another embodiment, the pharmaceutical compositions containing the proanthocyanidin polymer composition alternatively include one or more substances that either neutralize stomach acid and/or enzymes or are active to prevent secretion of stomach acid. These formulations can be prepared by methods known in the art, see, e.g., methods described in *Remington's Pharmaceutical Sciences,* 18th Ed., ed. Alfonso R. Gennaro, Mack Publishing Co., Easton, Pa., 1990.

The proanthocyanidin polymer composition can be provided in any therapeutically acceptable pharmaceutical form. The pharmaceutical composition can be formulated for oral administration as, for example but not limited to, drug powders, crystals, granules, small particles (which include particles sized on the order of micrometers, such as microspheres and microcapsules), particles (which include particles sized on the order of millimeters), beads, microbeads, pellets, pills, microtablets, compressed tablets or tablet triturates, molded tablets or tablet triturates, and in capsules, which are either hard or soft and contain the composition as a powder, particle, bead, solution or suspension. The pharmaceutical composition can also be formulated for oral administration as a solution or suspension in an aqueous liquid, as a liquid incorporated into a gel capsule or as any other convenient formulation for administration, or for rectal administration, as a suppository, enema or other convenient form. The proanthocyanidin polymeric composition can also be provided as a controlled release system (see, e.g., Langer, 1990, *Science* 249: 1527-1533).

The pharmaceutical formulation can also include any type of pharmaceutically acceptable excipients, additives or vehicles. For example, but not by way of limitation, diluents or fillers, such as dextrates, dicalcium phosphate, calcium sulfate, lactose, cellulose, kaolin, mannitol, sodium chloride, dry starch, sorbitol, sucrose, inositol, powdered sugar, bentonite, microcrystalline cellulose, or hydroxypropylmethylcellulose may be added to the proanthocyanidin polymer composition to increase the bulk of the composition. Also, binders, such as but not limited to, starch, gelatin, sucrose, glucose, dextrose, molasses, lactose, acacia gum, sodium alginate, extract of Irish moss, panwar gum, ghatti gum, mucilage of isapgol husks, carboxymethylcellulose, methylcellulose, polyvinylpyrrolidone, Veegum and starch arabogalactan, polyethylene glycol, ethylcellulose, and waxes, may be added to the formulation to increase its cohesive qualities. Additionally, lubricants, such as but not limited to, talc, magnesium stearate, calcium stearate, stearic acid, hydrogenated vegetable oils, polyethylene glycol, sodium benzoate, sodium acetate, sodium chloride, leucine, carbowax, sodium lauryl sulfate, and magnesium lauryl sulfate may be added to the formulation. Also, glidants, such as but not limited to, colloidal silicon dioxide or talc may be added to improve the flow characteristics of a powdered formulation. Finally, disintegrants, such as but not limited to, starches, clays, celluloses, algins, gums, crosslinked polymers (e.g., croscarmelose, crospovidone, and sodium starch glycolate), Veegum, methylcellulose, agar, bentonite, cellulose and wood products, natural sponge, cation-exchange resins, alginic acid, guar gum, citrus pulp, carboxymethylcellulose, or sodium lauryl sulfate with starch may also be added to facilitate disintegration of the formulation in the intestine.

In a preferred embodiment, the proanthocyanidin polymer composition formulation contains a directly compressible proanthocyanidin polymer composition but no excipients, additives or vehicles other than an enteric coating; however, the formulation may contain a lubricant, such as but not limited to, magnesium stearate. Preferably, the directly compressed proanthocyanidin polymer composition formulation is formulated as a tablet of pharmaceutically acceptable hardness (greater than 6 kp, preferably 8-14 kp, and more preferably 10-13 kp) and friability (not more than 1% loss in weight, preferably less than 0.8% loss in weight, and more preferably less than 0.5% loss in weight).

In another preferred embodiment of the invention, the proanthocyanidin polymer composition is formulated with a substance that protects the proanthocyanidin polymer composition from the stomach environment. In a more preferred embodiment, the proanthocyanidin composition is enteric coated. Enteric coatings are those coatings that remain intact in the stomach, but will dissolve and release the contents of the dosage form once it reaches the small intestine. A large number of enteric coatings are prepared with ingredients that have acidic groups such that, at the very low pH present in the stomach, i.e. pH 1.5 to 2.5, the acidic groups are not ionized and the coating remains in an undissociated, insoluble form. At higher pH levels, such as in the environment of the intestine, the enteric coating is converted to an ionized form, which can be dissolved to release the proanthocyanidin polymer composition. Other enteric coatings remain intact until they are degraded by enzymes in the small intestine, and others break apart after a defined exposure to moisture, such that the coatings remain intact until after passage into the small intestines.

Polymers which are useful for the preparation of enteric coatings include, but are not limited to, shellac, starch and amylose acetate phthalates, styrene-maleic acid copolymers, cellulose acetate succinate, cellulose acetate phthalate (CAP), polyvinylacetate phthalate (PVAP), hydroxypropylmethylcellulose phthalate (grades HP-50 and HP-55), ethylcellulose, fats, butyl stearate, and methacrylic acid-methacrylic acid ester copolymers with acid ionizable groups ("EUDRAGIT™"), such as "EUDRAGIT™ 30D", "EUDRAGIT™ RL 30D", "EUDRAGIT™ RS 30D", "EUDRAGIT™ L 100-55", and "EUDRAGIT™ L 30D-55". In a preferred embodiment, the pharmaceutical composition contains a proanthocyanidin polymeric composition and the enteric coating polymer "EUDRAGIT™ L 30D", an anionic copolymer of methacrylic acid and methyl acrylate with a mean molecular weight of 250,000 Daltons. In another preferred embodiment, the enteric coating polymer is "EUDRAGIT™ L 30D-55".

The disintegration of the enteric coating occurs either, by hydrolysis by intestinal enzymes or by emulsification and dispersion by bile salts, depending upon the type of coating used. For example, esterases hydrolyze esterbutyl stearate to butanol and stearic acid and, as the butanol dissolves, the stearic acid flakes off of the medicament. Additionally, bile salts emulsify and disperse ethylcellulose, hydroxypropylmethylcellulose, fats and fatty derivatives. Other types of coatings are removed depending on the time of contact with moisture, for example coatings prepared from powdered carnauba wax, stearic acid, and vegetable fibers of agar and elm bark rupture after the vegetable fibers absorb moisture and swell. The time required for disintegration depends upon the thickness of the coating and the ratio of vegetable fibers to wax.

Application of the enteric coating to the proanthocyanidin polymer composition can be accomplished by any method known in the art for applying enteric coatings. For example, but not by way of limitation, the enteric polymers can be applied using organic solvent based solutions containing from 5 to 10% w/w polymer for spray applications and up to 30% w/w polymer for pan coatings. Solvents that are commonly in use include, but are not limited to, acetone, acetone/ethyl acetate mixtures, methylene chloride/methanol mixtures, and tertiary mixtures containing these solvents. Some enteric polymers, such as methacrylic acid-methacrylic acid ester copolymers can be applied using water as a dispersant. The volatility of the solvent system must be tailored to prevent sticking due to tackiness and to prevent high porosity of the coating due to premature spray drying or precipitation of the polymer as the solvent evaporates.

Furthermore, plasticizers can be added to the enteric coating to prevent cracking of the coating film. Suitable plasticizers include the low molecular weight phthalate esters, such as diethyl phthalate, acetylated monoglycerides, triethyl citrate, polyethyl glycoltributyl citrate and triacetin. Generally, plasticizers are added at a concentration of 10% by weight of enteric coating polymer weight. Other additives such as emulsifiers, for example detergents and simethicone, and powders, for example talc, may be added to the coating to improve the strength and smoothness of the coating. Additionally, pigments may be added to the coating to add color to the pharmaceutical formulation.

In preferred embodiments, the pharmaceutical composition of the proanthocyanidin polymer composition is provided as enteric coated beads in hard-shell gelatin capsules. In a preferred embodiment, the proanthocyanidin polymer beads are prepared by mixing a proanthocyanidin polymer composition with hydroxypropylmethylcellulose and layering the mixture onto nonpareil seeds (sugar spheres). In a more preferred embodiment, the proanthocyanidin polymer composition that is directly compressible (e.g., as determined by the assays described in Section 5.1 supra and Section 10 infra and isolated e.g., as described in Section 10, infra), without any excipients, additives or vehicles other than an enteric coating is milled and fractionated into beads (i.e., as beads that do not contain the nonpareil sugar seeds). The beads may be covered with a seal coat of Opadry Clear (mixed with water). A preferred enteric coating for the proanthocyanidin polymer composition beads is "EUDRAGIT™ L 30D" or "EUDRAGIT™ L 30D-55" applied as an aqueous dispersion containing 20%-30% w/w dry polymer substance, which is supplied with 0.7% sodium lauryl sulfate NF (SLS) and 2.3% polysorbate 80 NF (Tween 20) as emulsifiers, to which plasticizers, such as polyethylene glycol and/or citric acid esters, are added to improve the elasticity of the coating, and talc can be added to reduce the tendency of the enteric coating polymer to agglutinate during the application process and to increase the smoothness of the film coating.

The final composition of a preferred formulation of the enteric coated proanthocyanidin polymer composition beads containing the nonpareil seeds is 17.3% w/w nonpareil seeds, 64.5% w/w proanthocyanidin polymer composition, 1.5% w/w hydroxypropylmethylcellulose, 0.5% w/w Opadry clear, 14.5% w/w "EUDRAGIT™ L 30D", 1.45% w/w triethyl citrate, and 0.25% w/w glyceryl monostearate. This pharmaceutical formulation may be prepared by any method known in the art or by the method described in Section 8.1, infra.

A preferred formulation of the proanthocyanidin polymer composition beads not containing the nonpareil seeds is 78% w/w directly compressible proanthocyanidin polymer composition (e.g., isolated by the method described in Section 10 infra), 0.76% w/w Opadry Clear, 19% w/w "EUDRAGIT™ L 30D-55", 1.9% triethyl citrate, and 0.34% w/w glyceryl monostearate. This pharmaceutical formulation may be prepared by any method known in the art or by the method described in Section 8.2, infra.

Another preferred formulation contains 54.58% w/w proanthocyanidin polymer composition beads (without nonpareil seeds and made of a directly compressible proanthocyanidin polymer composition), 1.78% w/w Opadry Clear, 39% w/w "EUDRAGIT™ L 30D-55", 3.9% triethylcitrate, and 0.74% w/w glyceryl monostearate.

In another preferred embodiment, the pharmaceutical composition of the proanthocyanidin polymer composition is formulated as enteric coated granules or powder (microspheres with a diameter of 300-500μ) provided in either hard shell gelatin capsules or suspended in an oral solution for pediatric administration. The enteric coated proanthocyanidin polymer composition powder or granules may also be mixed with food, particularly for pediatric administration. This preparation may be prepared using techniques well known in the art, such as the method described in Section 8.3, infra.

In general, the proanthocyanidin polymer composition granules and powder can be prepared using any method known in the art, such as but not limited to, crystallization, spray-drying or any method of comminution, preferably using a high speed mixer/granulator. Examples of high speed mixer/granulators include the "LITTLEFORD LODIGE™" mixer, the "LITTLEFORD LODIGE™" MGT mixer/granulator, and the "GRAL™" mixer/granulator. During the high-shear powder mixing, solutions of granulating agents, called binders, are sprayed onto the powder to cause the powder particles to agglomerate, thus forming larger particles or granules. Granulating agents which are useful for preparing the proanthocyanidin polymer composition granules, include but are not limited to, cellulose derivatives (including carboxymethylcellulose, methylcellulose, and ethylcellulose), gelatin, glucose, polyvinylpyrrolidone (PVP), starch paste, sorbitol, sucrose, dextrose, molasses, lactose, acacia gum, sodium alginate, extract of Irish moss, panwar gum, ghatti gum, mucilage of isapol husks, Veegum and larch arabogalactan, polyethylene glycol, and waxes. Granulating agents may be added in concentrations ranging from 1 to 30% of the mass of the particles or granules.

The proanthocyanidin polymer composition powder or granules are preferably coated using the fluidized bed equipment. The granules or powder may then be covered with a seal coat of Opadry Clear (mixed with water). A preferred enteric coating for the proanthocyanidin polymer composition is "EUDRAGIT™ L 30D" applied as an aqueous dispersion containing 30% w/w dry polymer substance, which is supplied with 0.7% sodium lauryl sulfate NF (SLS) and 2.3% polysorbate 80 NF (Tween 20) as emulsifiers, to which the plasticizers, polyethylene glycol and citric acid esters, are added to improve the elasticity of the coating, and talc is added to reduce the tendency of the enteric coating polymer to agglutinate during the application process and to increase the smoothness of the film coating. The final composition of the enteric coated powder is 81.8% w/w proanthocyanidin polymer composition, 1.5% w/w hydroxypropylmethylcellulose, 0.5% w/w Opadry clear, 14.5% w/w "EUDRAGIT™ L 30D", 1.45% w/w triethyl citrate, and 0.25% w/w glyceryl monostearate. The final composition of the enteric coated granules is 81.8% w/w proanthocyanidin polymer composition, 10% polyvinylpyrrolidone, 1.5% w/w hydroxypropylmethylcellulose, 0.5% w/w Opadry clear, 14.5% w/w "EUDRAGIT™ L 30D", 1.45% w/w triethyl citrate, and 0.25% w/w glyceryl monostearate.

The enteric coated proanthocyanidin polymer composition granules or powder particles can further be suspended in a solution for oral administration, particularly for pediatric administration. The suspension can be prepared from aqueous solutions to which thickeners and protective colloids are added to increase the viscosity of the solution to prevent rapid sedimentation of the coated powder particles or granules. Any material which increases the strength of the hydration layer formed around suspended particles through molecular interactions and which is pharmaceutically compatible with the proanthocyanidin polymer composition can be used as a thickener, such as but not limited to, gelatin, natural gums (e.g., tragacanth, xanthan, guar, acacia, panwar, ghatti, etc.), and cellulose derivatives (e.g., sodium carboxymethylcellulose, hydroxypropylcellulose, and hydroxypropylmethylcellulose, etc.). Optionally, a surfactant such as Tween may be added to improve the action of the thickening agent. A preferred suspension solution is a 2% w/w hydroxypropylmethylcellulose solution in water containing 0.2% Tween.

The proanthocyanidin polymer composition can also be formulated as enteric coated tablets. In one embodiment, the proanthocyanidin polymer composition is granulated with any pharmaceutically acceptable diluent (such as those listed above) by the methods described above for preparing the proanthocyanidin polymer composition granules. Then, the granules are compressed into tablets using any method well known in the art, for example but not limited to, the wet granulation method, the dry granulation method or the direct compression method. Preferred diluents include, but are not limited to, microcrystalline cellulose ("AVICEL™ PH 200/300") and dextrates ("EMDEX™"). Additionally, disintegrants, such as those described above, and lubricants, such those described above, may also be added to the tablet formulation. A preferred tablet formulation contains 250 mg proanthocyanidin polymer composition, 7 mg of the disintegrant "AC-DI-SOL™" (cross linked sodium carboxymethylcellulose), 1.75 mg of the lubricant magnesium stearate and the weight of "AVICEL™ PH 200/300" necessary to bring the mixture up to 350 mg. The tablets are coated with an enteric coating mixture prepared from 250 grams "EUDRAGIT™ L 30 D-55", 7.5 grams triethyl citrate, 37.5 grams talc and 205 grams water. This formulation may be prepared by any method well known in the art or by the method described in Section 8.4, infra.

In a preferred embodiment, a directly compressible proanthocyanidin polymer composition (e.g., as determined by the assays described in Section 5.1, supra, and Section 10, infra, and isolated, e.g., as described in Section 10, infra) is made into granules by size reduction (e.g., as described above) and mixed with a lubricant, preferably, magnesium stearate. Then, the lubricated granules are compressed into tablets using any method well-known in the art, for example but not limited to, the direct compression method. Preferably, each tablet is 125 mg containing 99.6% w/w directly compressible proanthocyanidin polymer composition and 0.40% w/w magnesium stearate. The tablets are then preferably coated with an enteric coating mixture of a 30% suspension (6.66 g in 22.22 g) of "EUDRAGIT™ L 30D-55", 0.67 g triethyl citrate, 1.67 g talc and 20.44 g purified water, per 100 grams of tablet. The tablets can be prepared by any method known in the art or by the method described in Section 8.5, infra.

In a more preferred embodiment, a directly compressible proanthocyanidin polymer composition is formulated into core tablets of either 250 mg or 500 mg containing 99.6% w/w directly compressible proanthocyanidin polymer composition and 0.40% w/w magnesium stearate. The tablets are then preferably coated with an enteric coating mixture. The final composition of the tablets is 86.6% w/w directly compressible proanthocyanidin polymer composition, 0.4% magnesium stearate, 6.5% "EUDRAGIT™ L30D-55", 0.9% triethyl citrate, 2.87% talc, and 2.74% white dispersion. The tablets can be prepared by any method known in the art, for example but not limited to the method described in Section 8.6, infra.

The proanthocyanidin polymer composition formed into small particles (which include particles sized on the order of micrometers, such as microspheres and microcapsules), particles (which include particles sized on the order of millimeters), drug crystals, pellets, pills and microbeads can be coated using a fluidized-bed process. This process uses fluidized-bed equipment, such as that supplied by "GLATT™", "AEROMATIC™", "WURSTER™", or others, by which the proanthocyanidin polymer composition cores are whirled up in a closed cylindrical vessel by a stream of air, introduced from below, and the enteric coat is formed by spray drying it onto the cores during the fluidization time. To coat tablets or capsules, Accela-Cota coating equipment ("MANESTY™") can be used. By this process, the tablets or capsules are placed in a rotating cylindrical coating pan with a perforated jacket and spraying units are installed within the pan and the dry air is drawn in through the rotating tablets or capsules. Any other type of coating pan, such as the "COMPU-LAB™" pan, Hi-coates "GLATT™" immersion sword process, the "DRIAM™" Dricoater, "STEINBERG™" equipment, "PELLEGRINI™" equipment, or "WALTHER™" equipment can also be used.

In another preferred embodiment, the proanthocyanidin polymer composition is provided as a suppository for rectal administration. Suppositories can be formulated with any base substance which is pharmaceutically acceptable for the preparation of suppositories and which is compatible with the proanthocyanidin polymer composition. Because rectal administration does not expose the proanthocyanidin polymer composition to the stomach environment, the pharmaceutical formulations for rectal administration need not be formulated to protect the composition from the stomach environment. Suppository bases which may be used to prepare suppositories with the proanthocyanidin polymer composition include, but are not limited to, cocoa butter, glycerinated gelatin, hydrogenated vegetable oils, mixtures of polyethylene glycols or fatty acids of polyethylene glycols or glycol-surfactant combinations or nonionic surfactant materials (such as polyoxyethylene sorbitan fatty acid esters (Tweens), polyoxyethylene stearates, and mixtures of sorbitan fatty acid esters (Span and Arlacel)). However, because of the hydrophilic nature of the proanthocyanidin polymer composition, a hydrophilic base for the suppository is suggested. A preferred suppository formulation for the proanthocyanidin polymer composition is prepared from 91 grams glycerin, 9 grams sodium stearate, 5 grams purified water and can be 5% to 50,% w/w proanthocyanidin polymer composition. Alternatively, the suppository may contain 10 grams proanthocyanidin polymer composition, 20 grams gelatin, and 70 grams of glycerin. Suppositories prepared from the proanthocyanidin polymer composition can be shaped by any method known in the art, including but not limited to, compression molding, fusion, or, preferably, melt molding. A method for preparing suppositories from the proanthocyanidin polymer composition is described in Section 8.7, infra.

In another embodiment, the proanthocyanidin polymer composition is formulated with a compound or compounds which neutralize stomach acid. Alternatively, the pharmaceutical composition containing the proanthocyanidin polymer composition is administered either concurrent with or subsequent to administration of a pharmaceutical composition which neutralize stomach acid. Compounds, such as antacids, which are useful for neutralizing stomach acid include, but are not limited to, aluminum carbonate, aluminum hydroxide, bismuth subnitrate, bismuth subsalicylate, calcium carbonate, dihydroxyaluminum sodium carbonate, magaldrate, magnesium carbonate, magnesium hydroxide, magnesium oxide, and mixtures thereof.

In another embodiment, the proanthocyanidin polymer composition is administered with a substance that inactivates or inhibits the action of stomach enzymes, such as pepsin. Alternatively, the pharmaceutical composition containing the proanthocyanidin polymer composition is administered either concurrent with or subsequent to administration of a pharmaceutical composition active to inactivate or inhibit the action of stomach enzymes. For example, but not by way of limitation, protease inhibitors, such as aprotin, can be used to inactivate stomach enzymes.

In another embodiment, the proanthocyanidin polymer composition is formulated with a compound or compounds which inhibit the secretion of stomach acid. Alternatively, the pharmaceutical composition containing the proanthocyanidin polymer composition is administered either concurrent with or subsequent to administration of a pharmaceutical composition active to inhibit the secretion of stomach acid. Compounds which are useful for inhibiting the secretion of stomach acid include, but are not limited to, ranitidine, nizatidine, famotidine, cimetidine, and misoprostol.

5.3. Applications or Methods of Use

The proanthocyanidin polymer composition reduces chloride flux across intestinal epithelial cells and reduces fluid movement into the intestinal lumen which results in fluid loss and dehydration associated with secretory diarrhea. Thus, the pharmaceutical formulations and methods of the invention are useful in prophylactic and therapeutic applications against secretory diarrhea, particularly in preventing the dehydration and electrolyte loss that accompanies secretory diarrhea.

The pharmaceutical formulations of the proanthocyanidin polymer composition can be used therapeutically or prophylactically against any type of secretory diarrhea in either humans or animals. In a preferred embodiment, the pharmaceutical formulation is used to treat secretory diarrheas caused by enteric bacteria. These enteric bacteria include, but are not limited to, *Vibrio cholerae, E. coli*, including the enteropathogenic, enterotoxigenic, enteroadherent, enterohemorrhagic, or enteroinvasive types of *E. coli*, other *Vibrio* spp., *Campylobacter* spp., *Salmonella* spp., *Aeromonas* spp., *Plesiomonas* spp., *Shigella* spp., *Klebsiella* spp., *Citrobacter* spp., *Yersinia* spp., *Clostridium* spp., *Bacteriodes* spp., *Staphylococcus* spp., and *Bacillus* spp. This embodiment also includes the treatment of traveler's diarrhea.

In another embodiment, the pharmaceutical formulation is used to treat secretory diarrhea caused by protozoa, including but not limited to, *Giardia* and *Cryptosporidium* spp., particularly *Cryptosporidium parvum*.

In another embodiment, the pharmaceutical formulation is used to treat secretory diarrhea caused by non-infectious etiologies, such as but not limited to, non-specific diarrhea, inflammatory bowel syndrome, ulcerative colitis, and cancers and neoplasias of the gastrointestinal tract.

In another embodiment, the pharmaceutical formulations of the invention are used for the treatment of HIV-Associated Chronic Diarrhea in patients with AIDS. In yet another embodiment, the pharmaceutical formulation is used to treat diarrhea in infants or children, including but not limited to, diarrhea caused by rotavirus.

The pharmaceutical formulations of the invention can also be used to treat diarrhea in non-human animals, particularly in farm animals, such as but not limited to, bovine animals, swine, ovine animals, poultry (such as chickens), and equine animals, and other domesticated animals such as canine animals and feline animals. In particular the pharmaceutical formulations of the invention can be used to treat diarrheal disease in non-human animals, particularly food animals such as cattle, sheep and swine, caused by bacterial pathogens such as enterotoxigenic, enterohemorrhagic and other *E. coli, Salmonella* spp., *Clostridium perfringens, Bacteriodes fragilis, Campylobacter* spp., and *Yersinia enterocolitica*, protozoal pathogens, particularly *Cryptosporidium parvum*, and viral agents, particularly rotaviruses and coronaviruses, but also togavirus, parvovirus, calicivirus, adenoviruses, bredaviruses, and astroviruses.

Additionally, the pharmaceutical formulations of the invention may also be administered prophylactically to humans and non-human animals to prevent the development of secretory diarrhea. By way of example, but not by way of limitation, a proanthocyanidin polymer composition pharmaceutical formulation can be administered to tourists traveling to a country where there is a risk of travelers diarrhea at a time or times that are effective for preventing the disease. The pharmaceutical compositions of the invention can be administered to AIDS patients to prevent the occurrence of HIV-Associated Chronic Diarrhea. Also, the pharmaceutical compositions of the invention can be administered to children in a community threatened with cholera epidemic or rotavirus epidemic to prevent the spread of the disease. Likewise, the pharmaceutical compositions of the invention can be administered to farm animals, particularly young or recently weaned farm animals, to prevent the development of diarrheal disease.

When used according to the formulations and methods of the present invention as a treatment for secretory diarrhea, effective dosage ranges of the pharmaceutical formulations of the proanthocyanidin polymer composition for oral administration are in the range of 0.1 to 100 mg/kg per day, preferably about 0.1 to about 40 mg/kg per day, optionally 0.1 to 25 mg/kg per day, and also optionally 0.1 to 10 mg/kg per day. It should be appreciated that the appropriate dose will depend upon the type and severity of the secretory diarrhea. It has been found that human subjects can tolerate at least up to 2 grams of the proanthocyanidin polymer composition per day (25-30 mg/kg/day) for up to 2 days. It is believed that doses may exceed 40 mg/kg per day, optionally up to 100 mg/kg per day, if such dosages are necessary to treat the secretory diarrhea.

When used according to the formulations and methods of the present invention as a prophylaxis for secretory diarrhea, effective dosage ranges of the pharmaceutical formulations of the proanthocyanidin polymer composition for oral administration are in the range of 0.1 to 100 mg/kg per day, preferably about 0.1 to about 40 mg/kg per day, optionally 0.1 to 25 mg/kg per day, and also optionally 0.1 to 10 mg/kg per day. It should be appreciated that the appropriate dose will depend upon the type and severity of the secretory diarrhea to be prevented. It has been found that human subjects can tolerate at least up to 2 grams of the proanthocyanidin polymer composition per day (25-30 mg/kg/day) for up to 2 days. It is believed that doses may exceed 40 mg/kg per day, optionally up to 100 mg/kg per day, if such dosages are necessary to prevent the secretory diarrhea.

The proanthocyanidin polymer composition can be administered for treatment or prevention of secretory diarrhea in any therapeutically acceptable pharmaceutical form. The pharmaceutical composition can be administered orally, in the form of, such as but not limited to, drug crystals, granules, small particles (which include particles sized on the order of micrometers, such as microspheres and microcapsules), particles (which include particles sized on the order of millimeters) beads, microbeads, pellets, pills, microtablets, compressed tablets or tablet triturates, molded tablets or tablet triturates, and in capsules, which are either hard or soft and contain the composition as a powder, particle, bead, solution or suspension. The pharmaceutical composition can also be administered orally, as a solution or suspension in an aqueous liquid, as a liquid incorporated into a gel capsule or as any other convenient formulation for administration, or rectally, as a suppository, enema or other convenient form.

In a preferred embodiment, an enteric coated pharmaceutical composition containing the proanthocyanidin polymer composition is administered for the treatment or prevention of secretory diarrhea. In a more preferred embodiment, the enteric coated pharmaceutical composition is enteric coated tablets or beads of a directly compressible pharmaceutical composition, optionally containing a lubricant such as, but not limited to, magnesium stearate. Preferred enteric coated formulations include, enteric coated beads in a hard-shell gelatin capsule, enteric coated microspheres in a hard-shell gelatin capsule, enteric coated microspheres provided in a suspension or mixed with food, which preparations are particularly convenient for pediatric administration, and enteric coated compressed tablets. In another embodiment, a pharmaceutical composition containing the proanthocyanidin polymer composition and a compound which neutralizes stomach acid or inhibits the secretion of stomach acid is administered for the treatment of secretory diarrhea. In yet another embodiment, a pharmaceutical composition containing the proanthocyanidin polymer composition is administered either concurrent with or subsequent to administration of a pharmaceutical composition which either neutralizes stomach acid or inhibits the secretion of stomach acid for treatment of secretory diarrhea. The proanthocyanidin polymer composition can also be formulated as a suppository for rectal administration.

The pharmaceutical formulations of the invention can also be administered either alone or in combination with other agents for treatment or amelioration of secretory diarrhea symptoms such as rehydration agents, antibiotics, anti-motility agents, and fluid adsorbents, such as attapulgite.

The pharmaceutical formulations of the invention can also be incorporated into animal feed for us in treating secretory diarrhea in animals such as bovine animals, swine, ovine animals, poultry, equine animals, canine animals, and feline animals.

The following series of Examples are presented for purposes of illustration and not by way of limitation on the scope of the invention.

6. EXAMPLE

Effect of Simulated Gastric Fluid, Simulated Intestinal Fluid and Hydrochloric Acid on the Proanthocyanidin Polymer Composition from *C. lechleri*

After per-oral administration of the proanthocyanidin polymer composition from *C. lechleri*, neither the polymers nor derivatives of the polymers were detected in either human or animal plasma samples. However, polymers were detected and quantitated in plasma of animals following intravenous administration. This led to the hypothesis that the proanthocyanidin polymer composition, upon oral administration, is altered in the gastrointestinal tract and a species which is derived from the proanthocyanidin polymer composition but is not detectable by the HPLC method used, is then absorbed into the systemic circulation. A second possibility is that the proanthocyanidin polymer composition is absorbed intact in the gastrointestinal tract but is quickly transformed after absorption. There is yet another possibility that proanthocyanidin polymers of large molecular weight are not absorbed from either the stomach or the intestine.

Thus, this investigation was performed to gain an understanding of the effects of HCl, simulated gastric juice and simulated intestinal fluid on stability of the proanthocyanidin polymer composition from *C. lechleri*. These conditions were chosen to mimic the chemical conditions of the digestive tract. Incubation with HCl produced an approximately 25% reduction in the concentration of the proanthocyanidin polymer composition within several minutes. A similar reduction of 32% was observed within minutes after incubation of the proanthocyanidin polymer composition with simulated gastric fluid (SGF), and a 48% reduction was observed after 2 hours of incubation. The additional loss observed after incubation in simulated gastric fluid as compared with the loss observed after incubation in HCl, could be due to binding of the proanthocyanidin polymer composition to the pepsin in the simulated gastric fluid. When, after incubation in simulated gastric fluid, the proanthocyanidin polymer composition-simulated gastric fluid mixture was incubated with simulated intestinal fluid, no further significant reduction in concentration was observed.

6.1. Materials and Methods

Following per-oral administration, a drug is in contact with gastric fluid for approximately 2 to 3 hours before it passes to the duodenum where the gastric fluid and the drug are mixed rapidly with intestinal fluid. Therefore, to best mimic the in vivo conditions, the proanthocyanidin polymer composition was first incubated in simulated gastric fluid for 2 hours and then diluted with simulated intestinal fluid in the ratio of 1:1 and incubated for an additional 6 hours at 37° C. Additionally, the proanthocyanidin polymer composition was incubated in simulated gastric fluid (SGF), hydrochloric acid (HCl) or water at 37° C. Aliquots were taken from each treatment sample at different time intervals, and the amount of proanthocyanidin polymer composition was quantitated by HPLC.

Preparation of Test Mixtures and Samples:
1. Simulated Gastric Fluid (SGF) was prepared according to USP XX, p. 1105, by dissolving 2.0 g of sodium chloride and 3.2 g of pepsin (from porcine stomach mucosa, Sigma) in 7.0 ml hydrochloric acid and sufficient water (HPLC grade, Fisher) to make 1000 ml. This test solution had a pH of about 1.2.
2. Simulated intestinal Fluid (SIF) was prepared according to USP XX, p. 1105, by dissolving 6.8 g of monobasic potassium phosphate in 250 ml of water and adding 190 ml of 0.2 N sodium hydroxide and 400 ml of water. 10.0 g of pancreatin (from porcine pancreas, Sigma) was then added, mixed and the resulting solution was adjusted to pH 7.5±0.1 with 0.2 N NaOH. The solution was diluted with water to 1000 ml.
3. Hydrochloric acid (pH=1.7) was prepared by adding 800 µl of 12 N hydrochloric acid to 100 ml water.
4. Proanthocyanidin polymer stock solution was prepared by dissolving 1.0 g of the proanthocyanidin polymer composition from *C. lechleri* in 10 ml distilled water.

Procedure:

The proanthocyanidin polymer composition stock solution was diluted 1:20 (to a total volume of 10 ml) in SGF or in purified water. The test solutions were incubated in an oven at 37° C. and 1 ml aliquots taken while stirring at time intervals of 0.03, 0.5, and 2.0 hours. After the aliquots were centrifuged for 10 minutes at 14,000 rpm 700 µl of the supernatant was withdrawn and neutralized with N NaOH containing 50 mM dibasic sodium phosphate to a pH of 7.0±0.1. At the end of the 2 hour incubation period, SIF was added to the proanthocyanidin polymer composition in SGF in the ratio of 1:1 and the pH adjusted to 7.0±0.1. Aliquots were taken and processed as described above at 2, 2.5, 4 and 6 hours after the initial mixture with SGF. The neutralized supernatant was diluted 1:9 in tetrahydrofuran (HPLC grade, Fisher). The samples were assayed by HPLC on a Hewlett Packard 1050 High Performance. Liquid Chromatograph using a 5 m PLgel 500A column (Polymer Laboratories) (300×7.5 mm) and a 5 m guard column (50×7.5 mm), with a mobile phase of 95% tetrahydrofuran and 5% water, an injection volume of 50 ml, a flow rate of 1 ml/min and a run time of 11 minutes. The proanthocyanidin polymers were detected by assaying for UV absorption at a wavelength of 280 nm.

6.2. Results and Discussion

The HPLC method used for quantitating the proanthocyanidin polymer composition did not include derivitization or ion-exchange and measures the unbound or "free" proanthocyanidin polymers and not the proanthocyanidin polymers bound to protein. Additionally, the HPLC chromatography is based on size exclusion chromatography and thus detects changes in the molecular size (polymerization or degradation) of the proanthocyanidin polymers but not chemical alterations which do not affect the size or molar extinction coefficient at 280 nm.

Effect of HCl on the Proanthocyanidin Polymer Composition:

To test the effect of HCl (a major component of gastric fluid) on the proanthocyanidin polymer composition from *C. lechleri* in vitro, the proanthocyanidin polymer composition was incubated for 2 hours in HCl at pH 1.2. Samples were taken after 0.03, 0.5 and 2.0 hours of incubation and analyzed using HPLC. The peak area for the HPLC profile of the proanthocyanidin polymer composition after incubation in HCl was compared to the peak area for the profile of the proanthocyanidin polymer composition after incubation in water (Table 1).

TABLE 1

EFFECT OF HYDROCHLORIC ACID (PH = 1.7) ON THE PROANTHOCYANIDIN POLYMER COMPOSITION.

| Time, h | Sample #1 % Peak Area | Sample #2 % Peak Area | Average (n = 2) |
|---|---|---|---|
| 0.03 | 94 | 67 | 81 |
| 0.5 | 73 | 71 | 72 |
| 2.0 | 77 | 70 | 74 |

* % Peak area was calculated by dividing peak area of the profile of the proanthocyanidin polymer composition in the test-medium by peak area of the profile of the proanthocyanidin polymer composition in water (control) and multiplying by 100.

Results indicate that after 0.03 hours in HCl, the peak area of the proanthocyanidin polymer composition profile, i.e. the concentration of the proanthocyanidin polymer composition, was reduced by 19%. After 0.5 hours and 2.0 hours incubation with HCl, the peak area of the proanthocyanidin polymer profile was reduced by 28% and 26%, respectively. These results indicate that most of the decrease of the proanthocyanidin polymer composition due to HCl exposure occurred within the first 2-3 minutes of incubation.

FIG. 1 shows sample chromatograms of the proanthocyanidin polymer composition after incubation in water and in HCl for 0.03 hours, and in HCl for 2.0 hours. In addition to the obvious reduction in the area of the peak of the proanthocyanidin polymer profile after incubation for 2 hours in HCl, a noticeable shift in the retention time of the shoulder was observed. A possible interpretation of the observed shift in retention time of the shoulder from 5.8 to 6.2 min after incubation of the composition in HCl is that HCl breaks down the proanthocyanidin polymers into subunits of slightly lower molecular weight with retention times longer than the retention time of the parent compound.

Effects of SGF on the Proanthocyanidin Polymer Composition:

When the proanthocyanidin polymer composition from *C. lechleri* was added to SGF, the mixture formed an opaque red precipitate. To determine if the precipitate was due to pepsin or sodium chloride, the proanthocyanidin polymer composition was added at a final concentration of 5 mg/ml to either SGF without sodium chloride or to SGF without pepsin. After the samples were centrifuged at 14,000 rpm for 10 min, only the mixture containing pepsin was opaque red with precipitation, indicating that the precipitation is due to the interaction of the proanthocyanidin polymer composition with pepsin.

After a 2 minute (0.03 hour) incubation of the proanthocyanidin polymer composition solution in SGF, HPLC analysis showed an approximately 32% reduction in the peak area of the proanthocyanidin polymer profile. The samples taken 0.5 and 2.0 hours after incubation at 37° C. showed no further significant change the peak area of the proanthocyanidin polymer profile. Chromatograms of the proanthocyanidin polymer samples incubated for 2 minutes and 2 hours in SGF are presented in FIGS. 2 and 3, respectively, and the peak area data from this experiment are shown in Table 2.

TABLE 2

EFFECT OF SGF ON THE PROANTHOCYANIDIN POLYMER COMPOSITION IN VITRO.

| Time, h | Sample #1 % Peak Area | Sample #2 % Peak Area | Average (n = 2) |
|---|---|---|---|
| 0.03 | 59 | 76 | 68 |
| 0.5 | 70 | 67 | 69 |
| 2.0 | 54 | 49 | 52 |
| 6.0 | 45 | 55 | 50 |

% Peak Area was calculated by dividing peak area of the profile of the proanthocyanidin polymer composition in the test-medium by peak area of the profile of the proanthocyanidin polymer composition in water (control) and multiplying by 100.

Most of the reduction in the concentration of the proanthocyanidin polymers occurred within 2 minutes of exposure to SGF. Furthermore, the decrease in the proanthocyanidin polymer composition detected by the HPLC assay might be due to a combination of the effects of degradation by the acid in the SGF and binding to the pepsin in the SGF.

The rapid decrease in peak area under the curve following the addition of the proanthocyanidin polymer composition to SGF solution is demonstrated in FIGS. 4 and 5 which show sample chromatograms of the proanthocyanidin polymer composition after 2 minutes and 2 hours of incubation in SGF respectively.

Effect of SIF on the Proanthocyanidin Polymer Composition:

To better understand the fate of the proanthocyanidin polymer composition from *C. lechleri* in the small intestines, the effect of intestinal fluid on the proanthocyanidin polymer composition was investigated in vitro. To best mimic the in vivo conditions, the proanthocyanidin polymer composition was first incubated in simulated gastric fluid for 2 hours and then diluted with simulated intestinal fluid in the ratio of 1:1 and incubated for an additional 6 hours at 37° C. Samples withdrawn at various time intervals following addition of SIF to the proanthocyanidin polymer composition-SGF solution were analyzed by HPLC. Representative chromatograms are presented in FIGS. 4 and 5. The results are shown in Table 3 and FIG. 6 and indicate that SIF did not significantly reduce the amount of proanthocyanidin polymer composition.

TABLE 3

INTERACTION OF SIF WITH SGF-PROANTHOCYANIDIN POLYMER COMPOSITION MIXTURE FOLLOWING 2 HOUR INCUBATION IN SGF FOLLOWED BY A 4 HOUR INCUBATION AFTER 1:1 DILUTION IN SIF.

| Time, h | Sample #1 % Peak Area | Sample #2 % Peak Area | Average (n = 2) |
|---|---|---|---|
| 2.0 | 44 | 52 | 48 |
| 2.5 | 50 | 42 | 46 |
| 4.0 | 59 | 45 | 52 |
| 6.0 | 45 | 55 | 50 |

% Peak Area was calculated by dividing peak area of the profile of the proanthocyanidin polymer composition in the test-medium by peak area of the profile of the proanthocyanidin polymer composition in water (control) and multiplying by 100.

6.3. Conclusion

The incubation conditions tested in this study mimic the conditions encountered by the proanthocyanidin polymer composition from *C. lechleri* following peroral administration. Some loss of the proanthocyanidin polymer composition (25-32%) was observed within minutes of incubation of the composition with dilute HCl and SGF. The greater loss observed after incubation in, SGF as compared to the loss after incubation in HCl could be caused by the binding of the proanthocyanidin polymer composition to the pepsin in the SGF. When the solution of the proanthocyanidin polymer composition in simulated gastric fluid was incubated with simulated intestinal fluid, no further significant reduction in the proanthocyanidin polymer composition was observed.

Because the method used to analyze the proanthocyanidin polymer composition was based on size exclusion chromatography, caution should be used in the interpretation of the results presented here because the method is unable to differentiate between native proanthocyanidin polymer composition and a proanthocyanidin polymer composition that has been chemically altered in a way that does not significantly change its size.

7. EXAMPLE

Assessment of the Effect of Enteric Coated Proanthocyanidin Polymer Composition on Fluid Accumulation in Cholera Toxin-Treated Mice The purpose of this study was to determine the effect of enteric-coated proanthocyanidin polymer composition prepared from *Croton lechleri* on fluid accumulation in the intestinal tract of mice treated with cholera toxin (CT). The pathophysiological mechanism by which cholera toxin produces fluid accumulation in mice is identical to the mechanism by which cholera toxin and other bacterial toxins produce fluid accumulation in humans. Reduction of the fluid in this model by a test compound indicates that the compound is useful as an antidiarrheal agent. At initial time ($t_o$), mice received cholera toxin (15 µg per average body weight of approximately 20 g) by oral gavage and were anorectally sealed with a cyano-acrylamide ester. Three hours later ($t_3$ h), a single dose of enteric coated proanthocyanidin polymer composition (131 mg/kg) suspended in 0.75% guar gum (vehicle) was administered by oral gavage. Water and a control solution consisting of an equivalent concentration of "EUDRAGIT™" and sugar in vehicle were also administered to two control groups. After a 7 hour ($t_7$ h) exposure to cholera toxin, mice were sacrificed and the entire murine intestinal tract from the pylorus to the rectum, including cecum, was isolated. The entire murine intestinal tract was isolated because, although fluid accumulation occurs in the small intestine, some fluid does leak into the large intestine. Fluid accumulation (FA) was measured as the ratio of the mass of accumulated fluid in the intestinal tract and rectum, including cecum, versus the mass of the intestinal tract minus the mass of the fluid. Under the experimental conditions, orally administered enteric coated proanthocyanidin polymer composition was shown to significantly reduce fluid accumulation in the intestinal tract of sealed adult mice treated with cholera toxin. Oral administration of enteric coated proanthocyanidin polymer composition (131 mg/kg) reduced the fluid accumulation ratio by an average of 45% and 38% compared to the mean fluid accumulation ratio in water controls and "EUDRAGIT™"/sugar/vehicle controls, respectively.

7.1. Preparation of Cholera Toxin and the Proanthocyanidin Polymer Compositions The following materials were obtained from commercial suppliers: cholera toxin (List Biological Lab, lot # CVX-48-3D); cyano-acrylamide ester (Borden Inc., Columbus, Ohio); animal feeding needles (Popper and Sons, Hyde Park, N.Y.); sodium bicarbonate (ACROS lot # 83559/1); guar gum (Sigma, lot # 94H0195); "EUDRAGIT™ L30D" (PMRS, lot # R10538); 40-60 mesh sugar spheres (PMRS, lot # R10542).

To prepare the cholera toxin stock solution, one milliliter of HPLC grade water (Mill Q) was added to a vial containing 1 mg of cholera toxin and two different vials were pooled and stored at 4° C. Cholera toxin solutions for administration to animals were freshly prepared by diluting 240 µl cholera toxin stock solution with 560 µl 7% w/vol NaHCO₃. Final concentration of NaHCO₃ was 4.9%. Each mouse received 15 µg of cholera toxin, in 50 µl volume by oral gavage at initial time ($t_o$).

The formulation for the enteric coated proanthocyanidin polymer composition from *C. lechleri* contained 17.3% (w/w) of nonpareil seeds (sugar spheres, 46/60 mesh) (Paulaur, lot # 60084060), 64.6% proanthocyanidin polymer composition, 1.5% hydroxypropylmethylcellulose (HPMC, Dow Chemical Co., lot # MM9410162E), 0.5% Opadry Clear (Colorcon, lot # S835563), 14.5% "EUDRAGIT™ L 30D" (Rohm Tech., lot # 1250514132), 1.45% triethyl citrate (Morflex, lot # N5×291), glyceryl monostearate (Rohm Tech, lot # 502-229), and purified water (USP).

The solution for layering the proanthocyanidin polymer composition onto the sugar spheres was prepared by adding HPMC and the proanthocyanidin polymer composition to purified water (USP) and mixing until dissolved. The nonpareil seeds were loaded into the product bowl of the fluid bed processor (Niro-Precision Coater). The proanthocyanidin polymer composition/HPMC solution was then sprayed onto fluidized nonpareil seeds, while maintaining the target bed temperature at 30-35° C. The layering process was continued until all the solution had been applied. Once the proanthocyanidin polymer composition layering had been completed, a seal coat of Opadry Clear (prepared by mixing the Opadry Clear with Purified Water, USP) was applied, maintaining the target bed temperature at 30-35° C. When the seal coat had been applied, the pellets were discharged and screened through 1000μ and 425μ screens and the layered spheres larger than 425μ and smaller than 1000μ were charged back into fluid bed processor. Meanwhile, the enteric coating solution was prepared by adding triethyl citrate and glyceryl monostearate to water that had been heated to 65° C. with continued mixing. This solution was added to the "EUDRAGIT™ L 30D-55" while mixing. The resulting enteric coating solution was then sprayed onto the layered spheres in the fluidized bed processor, at a bed temperature of 30-35° C. until all enteric coating solution was layered on the beads.

To facilitate oral gavage and prevent instantaneous settling of the beads, a thickening agent, guar gum was used. One hundred ml of 0.7% guar gum was prepared and adjusted to pH 2 with 2 ml of 0.5 M HCl. The enteric coated proanthocyanidin polymer composition beads were suspended in 0.7% guar gum solution. A control solution consisting of equivalent final concentrations of "EUDRAGIT™" and sugar was also prepared in 0.7% guar gum solution.

7.2. Methods and Results

The experiments were performed according to Richardson and Kuhn, 1986, *Infect. and Immun.* 54: 522-528. 50- to 52-day-old male mice with body masses that ranged from 15.7 to 18.7 g were used. Test animals were wild type C57Bl/6 mice and were obtained from Charles River Lab. All animals were maintained in metabolism cages with water ad libidum for the duration of the experiment. Mice were deprived of food for 24 hours prior to start of the experiment and during the course of experimentation. Initially ($t_o$ h), the mice received 15 μg cholera toxin by oral gavage and were anorectally sealed with a cyano-acrylamide ester (Superglue). Three hours later ($t_3$ h), the mice received by oral gavage either a suspension of the enteric coated proanthocyanidin polymer composition in guar gum solution or a control solution. After a 7 hour ($t_7$ h) exposure to cholera toxin, mice were sacrificed and the entire murine intestinal tract from the pylorus to the rectum, including cecum, was isolated. Care was taken to avoid tissue rupture and loss of fluid, and the attached mesentery and connective tissue were then removed. The mass of tissue and the fluid within was determined using an analytical balance. The tissue was then opened longitudinally, the fluid removed, and the tissue was patted dry. Fluid accumulation was measured as the ratio of the mass of accumulated fluid in the intestine (small and large including cecum) versus the mass of the intestine minus the mass of the fluid.

Statistical comparisons of the fluid accumulation ratio for different treatments were made by analysis of variance using Microsoft Excel (version 5.0). A p-value of $p<0.05$ was used to determine significance. Duncan's multiple range test as carried out to determine whether statistically significant reductions in cholera toxin-induced fluid accumulation ratios occurred in the mice that received the enteric coated proanthocyanidin polymer composition compared to animals that received only $H_2O$ or "EUDRAGIT™" plus sugar in 0.75% guar gum solution.

In the experiment described below, a total of 24 mice (8 ice per each treatment) were treated as follows:

Group A: Mice received cholera toxin at $t_0$ followed by a single dose of water at $t_3$ and were sacrificed at $t_7$ after administration of cholera toxin.

Group B: Mice received cholera toxin at $t_0$. At $t_3$, the mice received a single dose of enteric coated proanthocyanidin polymer composition (131 mg/kg body weight). The vehicle consisted of acidified 0.75% guar gum solution. All animals were sacrificed at $t_7$.

Group C: Mice received cholera toxin at $t_0$. At $t_3$, the mice received a single dose of an equivalent concentration of "EUDRAGIT™" and sugar (1.33 mg of "EUDRAGIT™" plus 1.046 mg of sugar/kg body weight). The vehicle consisted of acidified 0.75% guar gum solution. All animals were sacrificed at $t_7$.

Based on the preliminary studies which indicated the need for longer incubation time to assure complete transfer of the coated beads into the intestine, all animals were sacrificed at $t_7$ after cholera toxin dosing. To achieve more reliable results, the number of animals was increased to 8 mice for each group. Table 4 and FIG. 7 show the effect of enteric coated proanthocyanidin polymer composition on cholera toxin-induced fluid secretion in the sealed adult mouse model. As could be seen, a single dose of 131 mg proanthocyanidin polymer composition/kg significantly ($P<0.05$) reduced cholera toxin-induced fluid accumulation after a seven hour incubation with cholera toxin. Compared to the results after control treatments (groups A and C), enteric coated proanthocyanidin polymer composition beads (group B) significantly reduced the ratio of fluid accumulation by an average of 45% and 38% respectively.

In this experiment, none of the mice died as a result of treatment by oral gavage.

TABLE 4

THE EFFECT OF ENTERIC COATED PROANTHOCYANIDIN POLYMER COMPOSITION BEADS ON INTESTINAL FLUID ACCUMULATION IN CHOLERA TOXIN-TREATED MICE

| Group | No. of Mice | Treatment | Fluid Accumulation* (mg fluid/mg intestine) |
|---|---|---|---|
| A | 8 | $H_2O$ | 1.28 ± 0.09 a |
| B | 8 | 131 mg proanthocyanidin polymer composition in guar gum solution/kg | 0.71 ± 0.17 b |
| C | 8 | "EUDRAGIT ™" & sugar/guar gum solution | 1.15 ± 0.16 a |

*Values with different letters differ significantly ($p < 0.05$) by Duncan's Multiple Range Test.

Under the experimental conditions, enteric coated proanthocyanidin polymer composition significantly reduced fluid accumulation in the intestine of sealed adult mice treated with cholera toxin. Based on these results, oral administration of the enteric coated proanthocyanidin polymer composition (131 mg/kg) reduced the fluid accumulation ratio by an average of 38%, compared to the mean fluid accumulation ratio in "EUDRAGIT™" plus sugar controls.

Results of a further experiment using 18-20 mice per group are presented in FIG. 8 and Table 5, and these results confirm the results from the initial experiment. Mice in group B, which received 131 mg of the proanthocyanidin polymer composition/kg three hours ($t_3$) after exposure to cholera toxin, exhibited significant reduction in fluid accumulation as compared to mice which received "EUDRAGIT™" and sugar in water at $t_3$.

TABLE 5

THE EFFECT OF ENTERIC COATED PROANTHOCYANIDIN POLYMER COMPOSITION BEADS ON INTESTINAL FLUID ACCUMULATION IN CHOLERA TOXIN-TREATED MICE

| Grp. | No. of Mice | $t_0$ hr | $t_3$ hr | Fluid Accumulation (mg fluid/mg intestine) |
|---|---|---|---|---|
| A | 20 | CT/NaHCO$_3$ | "EUDRAGIT ™" & Sugar/H$_2$O | 1.34 ± 0.09 a* |
| B | 18 | CT/NaHCO$_3$ | 131 mg/kg proanthocyanidin polymer composition | 0.75 ± 0.10 b* |

*Values with different letters differ significantly (P < 0.001) by T-test.

8. EXAMPLE

Preparation of Pharmaceutical Formulations

Described below are illustrative methods for the manufacture and packaging for different preferred pharmaceutical formulations of the proanthocyanidin polymer composition from *C. lechleri* according to the present invention.

8.1. Encapsulated Enteric Coated Beads

Detailed descriptions of the batch formula and methods used to prepare the encapsulated enteric coated proanthocyanidin polymer composition bead formulation based on sugar spheres are provided below. Each hard-shell gelatin capsule contained 250 mg proanthocyanidin polymer composition enteric coated beads. Capsules were packaged in HDPE bottles containing sixteen (16) 250 mg caps each. The formulation for enteric coated proanthocyanidin polymer composition beads contained 17.3% (w/w) of nonpareil seeds (sugar spheres 40/60 mesh, Paulaur, lot #60084060), 64.5% proanthocyanidin polymer composition from *C. lechleri*, 1.5% hydroxypropylmethylcellulose (Methocel E5 Premium, Dow Chemical Co., lot #MM9410162E), 0.5% Opadry Clear (Colorcon, lot #S83563), 14.5% "EUDRAGIT™ L 30D" (Rohm Tech., lot #1250514132), 1.45% triethyl citrate (Morflex, lot #N5×291), glyceryl monostearate (Imwitor-900, Rohm Tech, lot #502-229), and purified water (USP).

The layering coating solution containing the proanthocyanidin polymer composition was prepared by adding hydroxypropylmethylcellulose and the proanthocyanidin polymer composition to purified water (USP) and mixing until dissolved. The nonpareil seeds were loaded into the product bowl of the fluid bed processor (Nior-Precision Coater). The polymer solution was then layered on the nonpareil seeds by spraying the solution onto the fluidized nonpareil seeds at a target bed temperature of 30-35° C. Once the proanthocyanidin polymer layering had been completed, a seal coat using Opadry Clear (preparing by mixing the Opadry Clear with Purified Water, USP) was applied with a target bed temperature of 30-35° C. After the seal coat was applied, the pellets were discharged and screened through 1000µ and 425µ screens, and the layered spheres larger than 425µ and smaller than 1000µ were charged back into the fluid bed processor. Meanwhile, the enteric coating solution was prepared by mixing triethyl citrate and glyceryl monostearate to water that had been heated to 65° C. and then mixing this solution with the "EUDRAGIT™ L 30D-55". The resulting enteric coating solution was then sprayed onto the layered spheres in the fluidized bed processor, at a bed temperature of 30-35° C., until all the enteric coating solution was layered on the beads. Based on the results of the HPLC assay indicating that the proanthocyanidin polymer composition was present at a concentration of 52.9%, the enteric coated beads were hand filled into a Size #0 hard shell gelatin capsule to provide a 250 mg dosage and then packaged into a suitable HDPE bottles with a heat induction lined cap.

TABLE 6

BATCH FORMULA
Product: Proanthocyanidin Polymer Enteric Coated Beads
Batch Size: 578.0 gm

| Raw Material | Amount Used Per Batch |
|---|---|
| Sugar Nonpareil Spheres, NF (40/60) | 100.0 gm |
| Proanthocyanidin Polymer Composition | 372.8 gm |
| Hydroxypropylmethylcellulose E5, USP (K29/32) | 8.7 gm |
| Opadry Clear (YS-1-19025A) | 2.9 gm |
| "EUDRAGIT ™ L 30D-55" (30% solids) | 279.4 gm |
| Triethyl Citrate, NF | 8.4 gm |
| Glycerol Monostearate | 1.4 gm |
| Water, USP (Removed during processing) | 1284.8 gm |

8.2. Encapsulated Enteric Coated Beads

Described below are the formula and methods used to prepare encapsulated enteric coated bead formulations that do not contain nonpareil sugar spheres. One formulation contains 83.3% w/w proanthocyanidin polymer composition, 0.5% w/w Opadry clear, 14.5% w/w "EUDRAGIT™ L 30D-55", 1.9% w/w triethyl citrate and a 0.34% glyceryl monostearate.

The beads were first seal coated with a 5% solution of Opadry clear in a 16 liter aeromatic MP-1 fluidized bed processor with a 50 mm Wurster column. The coating parameters for the application of the seal coating were an inlet temperature of 50° C. to 60° C., an outlet temperature of 25° C. to 40° C., an air volume of 30 to 40 CMH, a spray rate of 6 to 12 grams per minute, and an air pressure of 2.5, Bar. After the seal coat was applied, the beads were discharged and screened for beads larger than 425µ and smaller than 1000µ. The beads of appropriate size were then charged back into the fluid bed processes for enteric coating. For each 1000 grams of proanthocyanidin polymer composition beads, an enteric coating suspension was prepared from 811.97 grams "EUDRAGIT™ L 30D-55", 24.36 grams triethyl citrate, 4.36 grams glyceryl monostearate and 248.55 grams purified water. This suspension was prepared by gently stirring the "EUDRAGIT™ L 30D-55" suspension continually and, in a separate container, suspending and homogenizing the triethyl citrate and talc in purified water. The triethyl citrate/talc mixture was then added to the "EUDRAGIT™ L 30D-55" suspension, and the resulting coating dispersion stirred during the spraying process to avoid settling. The beads were then coated in the fluidized bed processor under the following parameters: The inlet temperature was 42° C. to 47° C.; the outlet temperature was 28° C. to 34° C.; the air volume was 30-40 CMH; the spray rate was 6-12 grams/minute; and the air pressure was 2.5

Bars. The resulting enteric coated beads were then filled into a size #0 hard shell gelatin capsule.

8.3. Enteric Coated Granules and Powder Particles

Described below is a method for formulating the proanthocyanidin polymer composition as enteric coated granules or powder (microspheres with a diameter of 300-500μ) in either hard shell gelatin capsules or suspended in an oral solution. The proanthocyanidin polymer composition powder particles are prepared by high-shear powder mixing of the proanthocyanidin polymer composition and hydroxypropylmethylcellulose in a high speed mixer/granulator. The proanthocyanidin polymer composition granules are prepared by spraying polyvinylpyrrolidone on the powder in the high speed mixer/granulator so that the powder particles agglomerate to form larger granules. Using fluidized bed equipment, the granules or powder are then covered with a seal coat of Opadry Clear (mixed with water) and then coated with the enteric coating "EUDRAGIT™ L 30D" applied as an aqueous dispersion containing 30% w/w dry methacrylate polymer substance, which is supplied with 0.7% sodium lauryl sulfate NF (SLS) and 2.3% polysorbate 80 NF (Tween 20) as emulsifiers, to which the plasticizers, triethyl citrate and glyceryl monostearate, are added to improve the elasticity of the coating. The final composition of the enteric coated powder is 81.8% w/w proanthocyanidin polymer composition, 1.5% w/w hydroxypropylmethylcellulose, 0.5% w/w Opadry clear, 14.5% w/w "EUDRAGIT™ L 30D", 1.45% w/w triethyl citrate, and 0.25% w/w glyceryl monostearate. The final composition of the enteric coated granules is 81.8% w/w proanthocyanidin polymer composition, 10% polyvinylpyrrolidone, 1.5% w/w hydroxypropylmethylcellulose, 0.5% w/w Opadry clear, 14.5% "EUDRAGIT™ L 30D", 1.45% w/w triethyl citrate, and 0.25% w/w glyceryl monostearate.

The enteric coated proanthocyanidin polymer composition granules or particles may be filled into a hard shell gelatin capsule in an amount which provides a suitable dosage.

The enteric coated proanthocyanidin polymer composition granules or powder particles can also be suspended in a solution for oral administration, particularly for pediatric administration. The suspension solution is prepared by wetting 2 grams hydroxypropylmethylcellulose in 97.8 ml distilled water and 0.2 grams Tween 80; mixing this preparation to homogeneity by sonicating, heating the solution to 40° C. and stirring for three hours; and then adding the enteric coated proanthocyanidin polymer composition powder particles or granules to the homogeneous solution.

8.4. Enteric Coated Compressed Tablets

A method for formulating the proanthocyanidin polymer composition with a diluent as enteric coated tablets is described below. For each 350 mg tablet, 250 mg proanthocyanidin polymer composition is granulated with 7 mg crosslinked sodium carboxymethylcellulose ("AC-DI-SOL™") and a sufficient mass of microcrystalline cellulose ("AVICEL™ PH 200/300") to bring the total mass to 350 mg. These ingredients are mixed for 20 to 30 minutes in a V blender. After the 20 to 30 minutes of mixing, 1.75 mg magnesium stearate is added and the mixture is blended for an additional 4 to 5 minutes. The resulting granules are compressed on a rotary tablet press using 5/16th inch standard concave punches. The tablets are coated with an enteric coating mixture prepared from 250 grams "EUDRAGIT™ L 30 D-55", 7.5 grams triethyl citrate, 37.5 grams talc and 205 grams water. The tablets are then placed in a perforated pan coater (e.g. the "ACCELA-COTA™" system) and rotated at 15 rpm at 40° C. The enteric coating formulation is sprayed using the following conditions: inlet air temperature of 44° C.-48° C., exhaust air temperature of 29° C.-32° C., product temperature of 26° C.-30° C., a 1 mm spray nozzle, a pan speed of 30 to 32 rpm, an airflow of 30-32 CFM, and a spray pressure of 20 PSI. The tablets are finally cured for 30 minutes as the pan is rotating at 15 rpm with an inlet air temperature of 60° C. and then, after shutting off the heat, the tablets are rotated at 15 rpm until the tablets have cooled to room temperature.

8.5. Enteric Coated Directly Compressed Tablets

A method for formulating the proanthocyanidin polymer composition without a diluent as enteric coated tablets was carried out as described below. Directly compressible proanthocyanidin polymer composition was produced according to the method described in Section 10, infra. 125 mg tablets were prepared by blending 99.6% w/w directly compressible proanthocyanidin polymer composition with 0.40% w/w magnesium stearate for two minutes and then directly compressing the material into 125 mg tablets on a rotary press using ¼ inch diameter round standard concave punches to a tablet hardness of 4-10 Kp.

The core tablets were tested and found to have an average hardness (n=10) of 4-10 Kp, friability (n=20) of less than 0.7%, an average table weight (n=10) of 125 mg±7 mg, an average thickness (n=10) of 3.9 to 4.1 mm, and a disintegration time (n=6) of not more than 20 minutes.

The coating dispersion was prepared by mixing, per 100 grams of tablets, 22.22 grams of a 30% w/w "EUDRAGIT™ L 30D-55" suspension, kept gently stirred with a mixture of 0.67 grams triethyl citrate, 1.67 grams talc and 20.44 grams purified water which had been mixed until homogeneous. The coating dispersion was continually stirred to avoid settling.

The tablets (in batches of 100,000) were coated with the coating dispersion in a Compu-Lab 24 inch/30 L pan. The tablets were jogged in the pan at a speed of 3-5 rpm and pre-warmed to a temperature of 35° C. to 40° C. The tablets were then coated with the enteric coating dispersion to a 6% to 8% weight gain with the following parameters: an inlet temperature of 45° C. to 65° C.; an exhaust air temperature of 27° C. to 34° C.; a product temperature of 28° C. to 32° C.; a pan speed of 8-14 rpm; an air flow of 180 to 240 CHM; an air spray pressure of 10-20 psi (pounds per square inch); an initial spray rate of 3 to 4 grams/min/kg; and a final spray rate of 4 to 8 grams/min/kg. The tablets were then cured for 30 minutes in the pan with an inlet temperature of 45° C. to 50° C. and a pan speed of 3 to 5 rpm. Finally, the tablets were allowed to cool to room temperature in the pan at a pan speed of 3 to 5 rpm. Four of the 125 mg tablets were then filled into a size zero, opaque Swedish orange-colored gelatin capsule.

The enteric coated proanthocyanidin polymer composition tablets were tested for content uniformity, drug release, microbiological tests and stability, and some analytical in process tests were also performed. In stability studies, the proanthocyanidin polymer composition remained stable after six months of storage at room temperature as well as under accelerated temperature and humidity conditions. Finally, the core tablets were tested and found to have an average hardness (n=10) of 4-10 Kp, friability (n=20) of less than 0.7%, an average tablet weight (n=10) of 125 mg±7 mg, an average thickness (n=10) of 3.9 to 4.1 mm, and a disintegration time (n=6) of not more than 20 minutes.

8.6. Enteric Coated Directly Compressed Tablets

Formulation of the proanthocyanidin polymer composition, without a diluent, as enteric coated tablets was carried out as described below. The directly compressible proanthocyanidin polymer composition was isolated as described in Section 10, infra. The core tablets were prepared by milling 250 mg proanthocyanidin polymer composition per tablet (approximately 16 kg total) in a Quadro Comil with an 024R (30 mesh) screen and then blending the milled composition in a Patterson Kelley 2 cubic foot twin shell blender. 1 mg magnesium stearate (Spectrum Quality Products, Inc., New Brunswick, N.J.) per tablet was then added to the composition in the blender and blended for 2 minutes. The blend was then compressed into 251 mg tablets (containing 250 mg proanthocyanidin polymer composition) on a rotary tablet press to a tablet hardness of 8-15 Kp and friability less than 0.5%.

The coating dispersion was prepared by first mixing in a first container the 25 g (7.5 g solids) "EUDRAGIT™ L 30 D-55" (Huls America, Inc., Somerset, N.J.) (weight given per 115 grams coated tablets) dispersion. The pigment dispersion was prepared by adding sequentially with constant stirring in a second container 39.59 g purified water, 3.30 grams talc (Alphafil™ 500) (Whittaker, Clark & Daniels, Inc., South Plainfield, N.J.), 6.06 g (3.15 g solids) White Dispersion (pigment) (Warner-Jenkinson, Inc., St. Louis, Mo.), and then 1.05 g triethyl citrate (Morflex, Inc., Greensboro, N.C.). The mixture was then homogenized for 15 minutes or until homogenous. While slowly stirring, the pigment dispersion was added to the "EUDRAGIT™ L 30 D-55" dispersion and then stirred for 30 minutes before spraying. Stirring was also maintained during the spraying process to avoid settling.

The tablets were coated in batches of 50,000 in a Compu-Lab 24 inch/30 L pan with the following settings: 10-20 psi atomizing air pressure; 35° C.-60° C. pan inlet air temperature; 5 to 6 inches nozzle tip to tablet bed distance; and 4/2 baffles/nozzles. After adding the tablets to the pan, the pan was jogged at a speed of 3 to 5 rpm and heated to 40° C. The tablets were then sprayed to a weight gain of 11 to 13% with the following parameters: 27°-33° C. target exhaust temperature (to be achieved within ten minutes of spraying); pan speed of 8 to 12 rpm; 180-240 CFM air flow; and a spray rate of 2-5 g/min/kg. After achieving the desired weight gain, the heat was shut off and the pan jogged at 3-5 rpm until the tablets were cooled to below 30° C.

The tablets were encapsulated in size AA opaque Swedish orange colored DB gelatin capsules (Capsugel, Greenwood, S.C.).

500 mg tablets were also produced as described above, except that coating was done on batches of 25,000 tablets to a weight gain of 8 to 10%.

8.7. Suppositories

Formulation of the proanthocyanidin polymer composition as a suppository for rectal administration is described below. One suppository formulation for the proanthocyanidin polymer composition can be prepared by heating 91 grams glycerin to 120° C., dissolving 9 grams sodium stearate in the heated glycerin, then adding 5 grams purified water. 5% to 50% proanthocyanidin polymer composition is added to the base and the mixture is then poured into a suitable mold. Alternatively, the suppository may be prepared by heating 20 grams gelatin and 70 grams glycerin to 70° C. and stirring for 2 hours, then adding 10 grams proanthocyanidin polymer composition which has been dissolved in purified water by sonicating for 5 minutes, and stirring at 40° C. until a homogeneous mixture is achieved. The preparation may then be poured into a mold suitable for preparing suppositories.

9. EXAMPLE

Effect of the Proanthocyanidin Polymer Composition Formulations in Patients Suffering from Traveler's or Non-Specific Diarrhea Summarized below are interim results obtained from the initial 20 patients of an open-label clinical trial of safety and effectiveness of the proanthocyanidin polymer composition from *C. lechleri* for the symptomatic treatment of acute non-specific diarrhea and traveler's diarrhea.

9.1. Human Safety and Efficacy Study

A total of 20 patients with traveler's diarrhea were entered into the study. The patient population consisted of young (average age=24 years) male and female patients who were students from the United States in Mexico. The students were recruited by the investigator as they entered the country and were told to report to the clinic after developing diarrhea and before starting any other medications.

Subjects were evaluated for the following parameters:
a) Usual stool frequency (number of stools per day or week).
b) Date and time of diarrhea onset.
c) Number of stools in the past 24 hours, categorized according to consistency as follows:
  Formed: retains its original shape in water
  Soft: assumes shape of the container
  Watery: can be poured
  (Stools of mixed form (e.g., soft/watery) were classified in the least formed category (e.g., watery)).
d) Symptoms experienced during the past 24 hours, including:
  Cramping
  Anal irritation
  Tenesmus
  Urgency (inability to delay timing by as long as 15 minutes)
  Fecal incontinence (decreased control of bowel movements)
  Inconvenience (interference with normal activities)
  Nausea
  Vomiting
  Increased intestinal gas After completion of the screening evaluations, samples for the baseline laboratory tests were obtained and the first dose of study medication was administered. The subjects were administered an initial loading dose of 1250 mg of the enteric coated proanthocyanidin polymer composition with three more doses of 250 mg every six hours for the first 24 hours of treatment, and then 500 mg four times per day for a total of 2 grams per day on the second day of dosage. The proanthocyanidin polymer composition was only administered for two days.

During the baseline clinic visit, the study participants were trained to accurately complete the diary and study forms, and the following evaluation parameters were considered:

1. Safety

Patients were asked about any adverse events experienced during the study. These events were categorized as to the severity, duration, relationship to study drug and any action taken. Blood and urine obtained at entry and at study completion were used to assess any changes.

2. Efficacy

Efficacy was assessed from the patient diary and clinic visits. The key efficacy parameters measured were the stool frequency, consistency and the time-to-last-unformed-stool.

9.2. Results

During the study, no significant adverse effects were observed in any of the subjects that could be attributed to the proanthocyanidin polymer composition. The primary efficacy parameters for this trial included self-reported stool frequency and time to last unformed stool. These data are summarized in Table 7.

TABLE 7

REPORTED STOOL FREQUENCY (20 PATIENTS TREATED)

| Time | Stools per Day (Mean) |
| --- | --- |
| 24 Hours prior to entry | 5.6 |
| Day 1 | 4.0 |
| Day 2 | 2.9 |
| Day 3 | 2.1 |
| Usual | 1.6 |

On average, the abnormal stool frequency trended toward normal over the three days of the study. The average number of stools per day returned to near-normal frequency by day 3. 4 patients returned to their normal stool frequency by the third study day. In addition, the time-to-last-unformed-stool was 30.3 hours on average.

Baseline and follow-up reports of gastrointestinal symptoms were obtained. Patients were asked to score the severity (mild, moderate or severe) of nine symptoms, including nausea, vomiting, cramping, gas, urgency, tenesmus, anal irritation, incontinence and inconvenience.

A total of 9 patients completely resolved their symptoms by the end of the 3 day study. Table 8 presents the number of patients who resolved all symptoms by the time indicated.

TABLE 8

RESOLUTION OF ALL SYMPTOMS BY TIME (20 PATIENTS TREATED)

| Time | Number of Patients Resolved |
| --- | --- |
| 24 hours | 1 |
| 48 hours | 2 |
| 60 hours | 4 |
| 72 hours | 2 |

A total score for the symptoms was obtained by assigning score of 0 to the absence of symptoms, 1 to mild, 2 to moderate and 3 to severe symptoms. The total scores for all patients at each time period were averaged and are presented in Table 9.

TABLE 9

SYMPTOM SCORE BY TIME (20 PATIENTS TREATED)

| Time | Average Score |
| --- | --- |
| Entry | 8.9 |
| 12 hours | 6.1 |
| 24 hours | 4.5 |
| 36 hours | 3.8 |
| 48 hours | 3.0 |
| 60 hours | 1.8 |
| 72 hours | 1.1 |

Based on our review of the data, we have reached the following conclusions:

1. While the drug was generally well tolerated, 3 patients experienced severe, self-limited nausea which was possibly related to study drug. However, none of the patients were withdrawn from the study due to an adverse event.

2. No significant changes in serum chemistry or hematology occurred during the treatment period. Six patients did experience mild changes in their urinalysis. We do not believe that these changes in urinalysis represent significant adverse effects. It was unclear if these changes were a result of the study drug or evolution of their underlying illness.

3. Stool frequency tended to return to normal frequency over the 3 day study period.

4. The average time-to-last-unformed-stool was 30.3 hours compared to a reported 69 hours in historical controls.

In summary, we further conclude that an enteric formulation of the proanthocyanidin polymer composition from *C. lechleri* is useful for the amelioration of stool frequency and gastrointestinal symptoms in patients afflicted by traveler's diarrhea. Overall the drug appears to be safe, with nausea being the most common event.

10. EXAMPLE

Isolation of Directly Compressible Proanthocyanidin Polymer Composition

A directly compressible proanthocyanidin polymer composition (used to prepare the formulations in Examples 8.5 and 8.6 above) was isolated from the latex of the *Croton lechleri* plant as follows:

460 liters of *Croton lechleri* latex was mixed with 940 liters purified water for ten minutes and then allowed to stand overnight (12 hours) at 4° C. The red supernatant was pumped into a holding tank and the residue discarded. The supernatant was then extracted with 200 liters n-butanol by mixing for ten minutes and then allowing the phases to separate. The n-butanol phase was discarded, and the aqueous phase was extracted two more times with 200 liters n-butanol each time. After extraction, the aqueous phase was concentrated by ultrafiltration using a 1 kD cut-off membrane (a low protein binding cellulose membrane), and then the retentate was dried in a tray dryer at approximately 37° C. (±2° C.).

For purification by column chromatography, 6 kg of the dried extract was dissolved in 75 liters of purified water and stirred for 90 minutes. The dissolved material was chromatographed on a two column chromatography system consisting of a 35 liter CM-Sepharose column (a weak cation exchange resin) and a 70 liter LH-20 column (a size-exclusion resin) connected in series. The material was loaded onto the CM-Sepharose column, washed with 140 liters purified water, and then eluted onto the LH-20 column with 375 liters of 30% acetone. At this point, the two columns were disconnected, and the proanthocyanidin polymer-composition was eluted from the LH-20 column with 250 liters of 45% liters acetone. Fractions were collected into 10 liter bottles and monitored with a UV detector at 460 nm. Fractions containing material having detectable absorbance at 460 nm were pooled and concentrated by ultrafiltration using a 1 kD cut-off membrane (a low protein binding cellulose membrane). The retentate was dried using a rotary evaporator in a waterbath at approximately 37° C. (±2° C.).

The proanthocyanidin polymer composition was tested for direct compressibility. 250 mg portions of the proanthocyanidin polymer composition, in the absence of any binders or excipients, was placed into a tableting machine and then pressed into tablets of varying thicknesses (i.e., the greater the pressure on the composition to form it into a tablet, the thinner the resulting tablet). The hardness of the tablets was then determined in a conventional hardness tester. FIG. 9 depicts the results of this test, demonstrating that increased pressure resulted in tablets of increased hardness. If a particular substance cannot be compressed into a tablet with integrity and a certain thinness (i.e., under a certain level of pressure), then the hardness cannot be determined because the tablet breaks apart during the measurement, i.e., the substance cannot be compressed into a tablet above a particular hardness value. Thus, the results in FIG. 9 demonstrate that the proanthocyanidin polymer composition isolated as described in this Section immediately above is directly compressible to hardness values appropriate for tablet formulations (i.e., greater than 6 kp, preferably 8-14 kp, more preferably 10-13 kp).

The friability of tablets having a hardness of 8-15 kp was determined as described in USP 23 <1216>. The friability was less than 0.5% loss in weight.

The invention described and claimed herein is not to be limited in scope by the specific embodiments herein disclosed since these embodiments are intended as illustrations of several aspects of the invention. Any equivalent embodiments are intended to be within the scope of this invention. Indeed, various modifications of the invention in addition to those shown and described therein will become apparent to those skilled in the art from the foregoing description. Such modifications are also intended to fall within the scope of the appended claims.

All publications cited herein are incorporated by reference in their entirety.

What is claimed is:

1. A method of treatment for secretory diarrhea in animals, including humans, said method comprising: administering, via the oral route of administration to a non-human animal selected from the group consisting of bovine, ovine, swine, poultry, equine, canine and feline animals or a human suffering from secretory diarrhea, a dosage of from 0.1 to 100 mg/kg/day of a pharmaceutical composition comprising an aqueous soluble proanthocyanidin polymer composition isolated from a *Croton* species or a *Calophyllum* species, said aqueous soluble proanthocyanidin polymer composition being in an amount effective to treat secretory diarrhea and formulated to protect the aqueous soluble proanthocyanidin polymer composition from the stomach environment in a controlled release preparation, and a pharmaceutically acceptable carrier.

2. The method of claim 1, in which the *Croton* species is *Croton lechleri*.

3. The method of claim 1, in which the pharmaceutical composition is formulated as a compressed tablet.

4. The method of claim 1, in which the pharmaceutical composition further comprises a lubricant.

5. The method of claim 4, in which the lubricant is magnesium stearate.

6. The method of claim 1, in which the pharmaceutical composition is formulated as a capsule, which capsule is enteric coated.

7. The method of claim 6, in which the capsule contains beads, each bead comprising a core of the proanthocyanidin polymer composition and a layer of the enteric coating.

8. The method of claim 1, in which the secretory diarrhea is caused by a bacterium.

9. The method of claim 1, in which the secretory diarrhea is caused by a non-infectious etiology.

10. The method of claim 9, in which the non-infectious etiology is selected from the group consisting of non-specific diarrhea, ulcerative colitis, and irritable bowel syndrome.

11. The method of claim 1, in which the human suffering from secretory diarrhea is an infant or a child.

12. The method of claim 1, in which the human is treated for HIV-Associated Chronic Diarrhea.

13. The method of claim 1, in which the human is treated for diarrhea caused by cholera.

14. The method of claim 1, in which a non-human animal is treated for secretory diarrhea.

15. The method of claim 14 in which the pharmaceutical composition is administered in animal feed.

16. The method of claim 1, in which dosage is between 0.1 and 40 mg/kg/day of the aqueous soluble proanthocyanidin polymer composition.

17. The method of claim 1, in which the pharmaceutical composition further comprises a pharmaceutically acceptable carrier.

18. A method of treatment for secretory diarrhea in animals, including humans, said method comprising: administering, via the oral route of administration, to a non-human animal or human suffering from secretory diarrhea, a dosage of from 0.1 to 100 mg/kg/day of a pharmaceutical composition comprising an aqueous soluble proanthocyanidin polymer composition isolated from a *Croton* species or from a *Calophyllum* species, said aqueous soluble proanthocyanidin polymer composition being in an amount effective to treat secretory diarrhea and coated with an enteric coating.

19. The method of claim 18, in which the *Croton* species is *Croton lechleri*.

20. The method of claim 18, in which the enteric coating is comprised of a methacrylic acid-methacrylic acid ester copolymer with acid ionizable groups.

21. The method of claim 18, in which the pharmaceutical composition is formulated as a compressed tablet.

22. The method of claim 18, in which the pharmaceutical composition further comprises a lubricant.

23. The method of claim 22, in which the lubricant is magnesium stearate.

24. The method of claim 18, in which the pharmaceutical composition is formulated as a capsule, which capsule is enteric coated.

25. The method of claim 24, in which the capsule contains beads, each bead comprising a core of the proanthocyanidin polymer composition and a layer of the enteric coating.

26. The method of claim 18, in which the secretory diarrhea is caused by a bacterium.

27. The method of claim 18, in which the secretory diarrhea is caused by a non-infectious etiology.

28. The method of claim 27, in which the non-infectious etiology is selected from the group consisting of non-specific diarrhea, ulcerative colitis, and irritable bowel syndrome.

29. The method of claim 18, in which the human suffering from secretory diarrhea is an infant or a child.

30. The method of claim 18, in which the human is treated for HIV-Associated Chronic Diarrhea.

31. The method of claim 18, in which the human is treated for diarrhea caused by cholera.

32. The method of claim 18, in which a non-human animal is treated for secretory diarrhea.

33. The method of claim 32, in which the non-human animal is selected from the group consisting of bovine, swine, ovine, poultry, equine, canine and feline animals.

34. The method of claim 32 in which the pharmaceutical composition is administered in animal feed.

35. The method of claim 18, in which said dosage of between 0.1 and 40 mg/kg/day of the aqueous soluble proanthocyanidin polymer composition.

36. The method of claim 18, in which the pharmaceutical composition further comprises a pharmaceutically acceptable carrier.

37. A method of treatment for secretory diarrhea in animals, including humans, said method comprising: administering, via the oral route of administration to a non-human animal selected from the group consisting of bovine, ovine, swine, poultry, equine, canine and feline animals or a human suffering from secretory diarrhea, a dosage of from 0.1 to 100 mg/kg/day of a pharmaceutical composition comprising an aqueous soluble proanthocyanidin polymer composition isolated from a *Croton* species or a *Calophyllum* species, said aqueous soluble proanthocyanidin polymer composition being in an amount effective to treat secretory diarrhea and formulated to protect the aqueous soluble proanthocyanidin polymer composition from the acidic conditions of the stomach in a controlled release preparation, and a pharmaceutically acceptable carrier.

* * * * *